(12) United States Patent
Peled et al.

(10) Patent No.: US 6,783,775 B2
(45) Date of Patent: *Aug. 31, 2004

(54) SERUM-DERIVED FACTOR INDUCING CELL DIFFERENTIATION AND MEDICAL USES THEREOF

(75) Inventors: Tony Peled, Mevaseret Zion (IL); Eitan Fibach, Mevaseret Zion (IL); Eliezer A. Rachmilewitz, Jerusalem (IL)

(73) Assignee: Hadasit Medical Research Services and Development Ltd., Jerusalem (IL)

( * ) Notice: Subject to any disclaimer, the term of this patent is extended or adjusted under 35 U.S.C. 154(b) by 267 days.

This patent is subject to a terminal disclaimer.

(21) Appl. No.: 09/986,503

(22) Filed: Nov. 9, 2001

(65) Prior Publication Data

US 2002/0054916 A1 May 9, 2002

Related U.S. Application Data

(63) Continuation of application No. 09/332,254, filed on Jun. 8, 1999, which is a continuation of application No. PCT/IL97/00395, filed on Dec. 1, 1997.
(60) Provisional application No. 60/032,646, filed on Dec. 10, 1996.

(51) Int. Cl.⁷ .............................................. A61K 35/16
(52) U.S. Cl. ...................... 424/531; 424/530; 424/529
(58) Field of Search ............................... 424/531, 530, 424/529

(56) References Cited

U.S. PATENT DOCUMENTS

| | | |
|---|---|---|
| 4,335,116 A | 6/1982 | Howard |
| 4,642,120 A | 2/1987 | Nevo et al. |
| 4,666,844 A | 5/1987 | Cheng |
| 4,820,531 A | 4/1989 | Tomes |
| 4,863,747 A | 9/1989 | Tomes |
| 4,932,992 A | 6/1990 | Radel |
| 4,935,000 A | 6/1990 | Dudek |
| 4,937,193 A | 6/1990 | Hinchliffe et al. |
| 4,952,607 A | 8/1990 | Sorenson et al. |
| 5,061,620 A | 10/1991 | Tsukamoto et al. |
| 5,071,872 A | 12/1991 | Witiak et al. |
| 5,073,492 A * | 12/1991 | Chen et al. ............... 435/240.2 |
| 5,120,831 A | 6/1992 | Pickart |
| 5,136,025 A | 8/1992 | Scheuermann et al. |
| 5,154,931 A | 10/1992 | Krueger et al. |
| 5,385,933 A | 1/1995 | Rabinovitz et al. |
| 5,472,863 A | 12/1995 | Maruta et al. |
| 5,472,867 A | 12/1995 | Kanz et al. |
| 5,486,359 A | 1/1996 | Caplan et al. |
| 5,545,418 A | 8/1996 | Iritani et al. |
| 5,547,692 A | 8/1996 | Iritani et al. |
| 5,565,491 A | 10/1996 | Schieven |
| 5,591,611 A | 1/1997 | Maruta et al. |
| 5,591,612 A | 1/1997 | Maruta et al. |
| 5,612,211 A | 3/1997 | Wilson et al. |
| 5,622,859 A | 4/1997 | Iritani et al. |
| 5,635,387 A | 6/1997 | Fei et al. |
| 5,637,323 A | 6/1997 | Wiltrout et al. |
| 5,650,147 A | 7/1997 | Wolpe et al. |
| 5,654,186 A | 8/1997 | Cerami et al. |
| 5,665,557 A | 9/1997 | Murray et al. |
| 5,674,750 A | 10/1997 | Kraus et al. |
| 5,674,843 A | 10/1997 | Carlino |
| 5,677,136 A | 10/1997 | Simmons et al. |
| 5,679,550 A | 10/1997 | Yoshimura et al. |
| 5,681,559 A | 10/1997 | DiGiusto et al. |
| 5,716,411 A | 2/1998 | Orgill et al. |
| 5,716,616 A | 2/1998 | Prockop et al. |
| 5,728,581 A | 3/1998 | Schwartz et al. |
| 5,733,541 A | 3/1998 | Taichman et al. |
| 5,736,396 A | 4/1998 | Bruder et al. |
| 5,763,261 A | 6/1998 | Gruenberg |
| 5,807,884 A | 9/1998 | Medford et al. |
| 5,925,567 A | 7/1999 | Kraus et al. |
| 6,372,262 B1 * | 4/2002 | Peled et al. ................. 424/531 |

FOREIGN PATENT DOCUMENTS

| | | |
|---|---|---|
| GB | 1304697 | 1/1973 |
| JP | 60-149529 | 8/1985 |
| WO | WO 00/11139 | 3/2000 |

OTHER PUBLICATIONS

Chen et al., Exp. Eye Res. 39(4): 469–378 (1984). Abstract.*
Steinkuhler et al., "Increase of Cu,Zn–Superoxide Dismutase Activity During Differentiation of Human K562 Cells Involves Activation by Copper of a Constantly Expressed Copper–deficient Protein", The Journal of Biological Chemistry, vol. 266, No. 36, pp. 24580–24587, Dec. 25, 1991.
Darwish et al., "Mobilization of Copper(II) from Plasma Components and Mechanism of Hepatic Copper Transport", The American Physiological Society, pp. 672–679, 1984.
Lehninger, "The Molecular Basis of Cell Structure and Function", Biochemistry, Second Edition, 1975, pp. 73–75.

(List continued on next page.)

Primary Examiner—Jean C. Witz
(74) Attorney, Agent, or Firm—Mintz, Levin, Cohn, Ferris Glovsky and Popeo, P.C.; Ivor R. Elrifi

(57) ABSTRACT

The present invention relates to a biologically active serum-derived composition of matter (SDF), having a low molecular weight, being electrically charged at acidic pH and having absorption at 280 nm. The molecular weight of said SDF was determined by electron spray mass spectrometry and is of 316 Da. SDF of the present invention or its complex with ceruloplasmin (CP) have several therapeutic properties. For example, SDF or its complex with CP is capable of inducing terminal cell differentiation of leukemic cells, which as a result, may lose their ability to proliferate and their ability for self cell renewal. Further, SDF or the complex with CP is capable of stimulating the proliferation of early, normal progenitor cells and inhibiting enhanced angiogenesis. In addition, SDF or its complex with CP is capable of ex vivo expanding normal stem and progenitor cells. The invention also relates to pharmaceutical composition comprising as active ingredient SDF or its complex and optionally further comprising pharmaceutically acceptable additives. Such pharmaceutical compositions may be for inhibiting enhance angiogenesis, for inducing remission of tumors, for maintaining tumor remission, and for expanding hematopoietic normal stem and progenitor bone marrow transplants.

9 Claims, 15 Drawing Sheets

OTHER PUBLICATIONS

Chomienne, Christine, et al., "Retinoid Differentiation Therapy in Promyelocytic Leukemia," *The FASEB Journal*, Jul. 1991, vol. 10, pp. 1025–1030.

Arogones, J., et al., "Dithiocarbamates Trigger Differentiation and Induction of CD11c Gene Through AP–1 in the Myeloid Lineage", *The Journal of Biological Chemistry*, May 3, 1996, vol. 271, No. 18, pp. 10924–10931.

Emerson, S.G., "Ex Vivo Expansion of Hematopoietic Precursors, Progenitors, and Stem Cells: The Next Generation of Cellular Therapeutics", *Blood*, Apr. 15, 1996, vol. 87, No. 8, pp. 3082–3088.

Protti, M.P., et al., "Particulate Naturally Processed Peptides Prime a Cytotoxic Response Against Human Melanoma in vitro", *Cancer Research 56*, Mar. 15, 1996, pp. 1210–1213.

Williams, S.F., et al., "Selection and Expansion of Peripheral Blood $CD34^+$ Cells in Autologous Stem Cell Transplantation for Breast Cancer", *Blood*, Mar. 1, 1996, vol. 87, No. 5, pp. 1687–1691.

Young, J.W., et al., "Identification of Dendritic Cell Colony–Forming Units Among Normal Human $CD34^+$ Bone Marrow Progenitors that are Expanded by c–*kit*–ligand and Yield Pure Dendritic Cell Colonies in the Presence of Granulocyte/Macrophage Colony–Stimulating Factor and Tumor Necrosis Factor", *The Rockefeller University Press*, Oct., 1995, vol. 182, pp. 1111–1119.

Brugger, W., et al., "Reconstitution of Hematopoiesis After High–Dose Chemotherapy by Autologous Progenitor Cells Generated by ex vivo", *The New England Journal of Medicine*, Aug. 3, 1995, vol. 333, No. 5, pp. 283–287.

Sandstrom, C.E., et al., "Effects on $CD34^+$ Cell Selection and Perfusion on ex vivo Expansion of Peripheral Blood Mononuclear Cells", *Blood*, Aug. 1, 1995, vol. 86, No. 3, pp. 958–970.

Ammendola, R., et al., "The DNA–Binding Efficiency of Spt is Affected by Redox Changes", May/Jul., 1994, pp. 483–489.

Bernhard, H., et al., "Generation of Immunostimulatory Dendritic Cells from Human $CD34^+$ Hematopoietic Progenitor Cells of the Bone Marroe and Peripheral Blood", *Cancer Research 55*, Mar. 1, 1995, pp. 1099–1104.

Walker, L.J., et al., "Identification of Residues in the Human DNA Repair Enzyme HAPI (Ref–1) that are Essential for Redox Regulation of Jun DNA Binding", *Molecular and Cellular Biology*, Sep. 1993, vol. 13, No. 9, pp. 5370–5376.

Koller, M.R., et al., "Large–Scale Expansion of Human Stem and Progenitor Cells from Bone Marrow Mononuclear Cells in Continuous Perfusion Cultures", *Blood*, Jul. 15, 1993, vol. 82, No. 2, pp. 378–384.

Naito, Y., et al., "Effects of Pyrroloquiniline Quinone (PQQ) and PQQ–Oxazole on DNA Synthesis of Cultured Human Fibroblasts," *Life Sciences*, 1993, vol. 52, No. 24, pp. 1909–1915.

Xanthoudakis, S., et al., "Redox Activation of FOS–JUN DNA Binding Activity is Mediated by a DNA Repair Enzyme", *The EMBO Journal*, 1992, vol. 11, No. 9, pp. 3323–3335.

Stern, R.V., et al., "A Tentacle Gel Simplifies the Purification of Ceruloplasmin", *Biochemistry International*, Jul. 1992, vol. 27, No. 21, pp. 281–289.

Folkman, J., "What is the Evidence that Tumors are Angiogenesis Dependent?", *Journal of the National Cancer Institute*, Jan. 3, 1990, vol. 82, No. 1, pp. 4–6.

Shabo, Y., et al., "The Myeloid Blood Cell Differentiation–Inducing Protein MGI–2A is Interleukin–6", *Blood*, Dec. 1988, vol. 72, No. 6, pp. 2070–2073.

Calabrese, L., et al., "Reexamination of Spectroscopic Properties of Ceruloplasmin Freshly Isolated with a Novel Very Rapid Single–Step Procedure", *Biochemistry International*, Feb., 1988, vol. 16, No. 2, pp. 199–208.

Breitman, T.R., et al., "Induction of Differentiation of the Human Promyelocytic Leukemia Cell Line (HL–60) by Retinoic Acid", *Proc. Natl. Acad. Sci. USA*, May, 1980, vol. 77, No. 5, pp. 2936–2940.

Shimizu, M., "Clinical Results on the Use of Human Ceruloplasmin in Aplastic Anemia", *Transfusion*, Nov./Dec., 1979, 19, No. 6, pp. 742–748.

Collins, S.J., et al., "Terminal Differentiation of Human Promyelocytic Leukemia Cells Induced by Dimethyl Sulfoxide and Other Polar Compounds", *Proc. Natl. Acad. Sci. USA*, May, 1978, vol. 75, No. 5, pp. 2458–2462.

Fibach, E., et al., "Control of Normal Differentiation of Myeloid Leukemic Cells: X1. Induction of a Specific Requirement for Cell Viability and Growth During the Differentiation of Myeloid Leukemic Cells", *Journal of Cellular Physiolo* Feb., 1976, vol. 89, pp. 259–266.

Fibache, E., et al., "Control of Normal Differentiation of Myeloid Leukemic Cells: VIII. Induction of Differentiation to Mature Granulocytes in Mass Culture", *Journal of Cellular Physiology*, Oct., 1975, vol. 86, No. 2, pp. 221–230.

Folkman, J., "Tumor Angiogenesis: Therapeutic Implications", *The New England Journal of Medicine*, Nov. 1, 1971, vol. 285, No. 21, pp. 1182–1186.

Hayashi, M. et al., "Control of Normal Differentiation of Myeloid Leukemic Cells V. Normal Differentiation in Aneuploid Leukemic Cells and the Chromosome Binding Pattern of $D^-$ and $D^+$ Clones", *International Journal of Cancer*, Mar. 6, 1974, vol. 14, pp. 40–48.

Inbar, M., et al., "Mobility of Carbohydrate–Containing Structures on the Surface Membrane and the Normal Differentiation of Myeloid Leukemic Cells to Macrophages and Granulocytes", *Proc. Natl. Acad. Sci. USA*, Sep. 1973, vol. 70, No. 9, pp. 2577–2581.

Fibache, E., et al., "Control of Normal Differentiation of Myeloid Leukemic Cells: IV. Induction of Differentiation by Serum From Endotoxin Treated Mice", *Journal of Cellular Physiology*, Apr., 1974, vol. 83, No. 2, pp. 177–185.

Fibache, E., et al., "Control of Normal Differentiation of Myeloid Leukemic Cells to Macrophages and Granulocytes", *Proc. Natl. Acad. Sci. USA*, Feb., 1973,, vol. 70, No. 2, pp. 343–346.

Fibache, E., et al., "Normal Differentiation of Myeloid Leukaemic Cells Induced by a Protein Differentiation Inducing Protein", *Nature New Biology*, Jun. 28, 1972, vol. 237, pp. 276–278.

Savyon–Healthcare, Stem Cell Culture Rights Claims by Aastrom, Clinica 785, Jul. 14, 1997, pp. 01.

Hogan et al., Engraftment and Development . . . Blood 1997, Jul. 1, 1990, (1) pp. 85–96.

Shpall E.J., The Utilization of Cytokines . . . , Bone Marrow Transplant, 1999, May 23, Suppl.

Nieto, Y, et al., Autologous stem–cell . . . , Hematal Oncol. Clin North Am, 1999, Oct. 13 (5), pp. 939–968.

Shpall et al., Peripheral Blood Stem Cell . . . , Baillieres Best . . . 1999, Mar.–Jun., 12 (1–2) pp. 219–232.

Howrey, RP et al., Graft–versus–leukemia–induced . . . Bone Marrow Transplant 2000, Dec. 26 (11) pp. 1251–1254.

Shpall E.J. et al, Purging of Autologous . . . , J. Hematother 1992 Spring, 1(1), pp. 45–54.
Shpall E.J. et al, Transplantation of . . . , J. Hematother 1994 Summer, 3(2), pp. 145–145.
Berenson, RJ et al., Transplantation of . . . Cancer Invest. 1996, 14 (6), pp. 589–596.
Cagnoni P.J., Mobilization and Selection . . . , Blood Rev 1996 Mar., 10 (1) pp. 1–7.
Shpall et al., Peripheral Blood Stem Cells . . . , Annu Rev Med 1997, 48, pp. 241–251.
Shpall et al., Effects of CD34+ . . . Biol Blood Marrow Transplant, 1998, 4 (2), pp. 84–92.
Hogan CJ et al., Multilineage Engraftment . . . Biol Blood Marrow Transplant, 1997, Nov, 3(5) pp. 236–246.
Shpall EJ, Stem Cell Isolation, Crur Opin Hematol, 1995, Nov. 2 (6) pp. 452–459.
Peters WP et al., Role of Cytokines . . , Hematol Oncol Clin North Am 1993, Jun., 7(3) pp. 737–747.
Kurtzberg J. Unrelated Placental Blood . . . Stem Cells 2000, 18(2), pp. 153–154.
Fraser J.K. et al, Cord Blood Transplantation Study . . . , J. Hematother 1998 Dec. 7, (6) pp. 521–561.
Rubinsten P. et al., Outcomes Among 562 . . . , N. Engl J. Med 1998, Nov. 26, 339 (22), pp. 1565–1577.
Kurtzberg J. et al., The Use of Umbilical . . . , Blood Cells 1994, 20 (2–3), pp. 275–2783, discussion 284.
Sugarman J., Ethical Aspects of Banking . . . , JAMA 1995 Dec 13, 274 (22), pp 1783–1785.
Kelly P., Umbilical Cord Blood Stem Cells . . . , J. Pediatr. 1997, May, 130 (5) pp. 695–703.
Klein A.K. et al., T–Cell Recovery in Adults . . . , Biol. Blood Marrow Transplant 2001, 7 (8) pp 454–466.
Gluckman E., Use of Hematopoetic . . . , Bull Acad. Mat'l Med. 1998, 182 (2), pp. 337–348.
Gluckman E. et al., Umbilical Cord Blood Transplants, Curr. Opin. Hematol, 2000, Nov.; 7 (6) pp. 353–357.
Gluckman E. et al., Results of Unrelated Umbilical Cord . . . , Rev. Clin. Exp. Hematol 2001, Jun., 5 (2) pp. 87–99.
Broxmeyer HE et al., Umbilical Cord Blood . . . , Blood Cells 1991, 17, (2), pp. 313–329.
Broxmeyer HE et al., Human Umbilical Cord Blood . . ., Int. J. Cell Cloning 1990, Jan, 8 Suppl. 1, pp. 76–89, discussion pp. 89–91.
Walters MC et al., Collaborative Multicenter . . . , Biol. Blood Marrow Transplant 1997, Dec. 3, (6), pp. 310–315.
Laursen pH et al., Synthesis of 2,4,7–trichloroimidao . . . , J. Am. Chem. Soc, Vol 27, Jul. 1962, pp. 2500–2504.
Beardsley T., Stern Cells Come of Age, on–line Scientific American, Jul. 1999, pp. 1–2.

Long–Term Expansion of Hemopoietic Progenitors (HPC) from Human Umbilical Cord Blood by Copper Chelators, presented at $41^{st}$ ASH Meeting, 1999, New Orleans, USA.
Regulation of Long–Term Expansion of Hemopoietic Stem–Progenator Cells (HPC) By Intracellular Copper Content, presented at $42^{nd}$ ASH Meeting, 2000, San Francisco, USA.
Involvement of Copper in Proliferation and Differentiation of Hemopoietic Progenitors, presented at $41^{st}$ ASH Meeting, 1999, New Orleans, USA.
Zhoa, J. et al., An Efficient Method for the Cryopreservation of Fetal Human Liver Hematopoeitic Progenitor Cells, Stem Cells 2001, 19, pp. 212–218.
Ohta Y. et al., Ascrobate–induced high–affinity . . . Biochem Biophys Res. Commun. 2001, Oct. 5, 287 (4), pp 888–894.
Aoki S., et al., A Double–Functionalized Cyclen . . . J. Am. Chem. Soc. 2001, Feb. 14, 123(6), pp 1123–1132.
Al–Abdullah IH et al., Neogenesis of Pancreatic Endocrine . . . , Pancreas 2000, Jul, 21 (1), pp. 63–68.
Kim SY et al., Macrocycles within Macrocycles . . . Angew Chem. Int. Ed. Engl. 2001, Jun. 1, 40 (11) pp. 2119–2121.
Jones–Wilson TM et al., The in–vivo Behavior of Copper–64–Labeled . . . , Nucl. Med. Biol. 1998, Aug. 25, (6) pp. 523–530.
Kimura E. et al., Why Zinc in Zinc Enzymes . . . , J. Biol. Inorg. Chem. 2000, Apr. 5, (2) pp. 139–155.
Inouye Y. et al., Inhibition of Human Immunodeficiency . . . , Biol, Pharm Bull, 1994, Feb., 17 (2), pp. 243–250.
Kikuta E. et al., Controlling Gene Expression . . . , J. Inorg. Biochem, 2000, Apr., 79 (1–4), pp. 253–259.
Bridger GJ et al., Synthesis and Structure Activity . . . , J. Med. Chem., 1996, Jan 5, 39 (1), pp. 109–119.
Inoyue Y. et al., Differential Contribution of Metal . . . , Biol. Pharm. Bull, 1996, Mar. 19(3) pp. 456–458.
Hyun HJ et al., Depletion of Intracellular Zinc and Copper . . . , Invest Opthalmol Vis Sci 2001, Feb; 42.
Pyatt DW et al., Dithiocarbamates Inhit . . . , Biochem Biophys. Res. Commun, 2000, Aug. 2, 274 (2), pp. 513–518.
Chen, SH et al., Oxidative Stress and c–Jun– . . . , Eur. J. Pharmacol, 2001, Mar 2, 414,(2–3), pp. 177–188.
Iseki A., et al., Pyrrolidine dithiocarbamate Inhibits . . . , Biochem Biophys Res. Commun. 2000, Sept. 16, 276(1) pp. 88–92.
Cox C. et al., The Role of Copper Suppression . . . , Laryngoscope 2001, Apr. 111(4 Pt 1), pp 696–701.
Thaler F. et al., Structural, Spectroscopic . . . , Inorg Chem 1998, Aug. 10, 37(16), pp. 4022–4029.
Chelators for Iron Overload, Oct. 8, 1999, pp. 1–5.

* cited by examiner

SERUM-DERIVED FACTOR INDUCING CELL DIFFERENTIATION AND MEDICAL USES THEREOF

RELATED PATENT APPLICATIONS

This is a continuation of U.S. patent application Ser. No. 09/332,254 filed Jun. 8, 1999, which application is still pending which is a continuation of PCT Application Serial No. PCT/IL97/00395 filed Dec. 1, 1997 which claims priority from Provisional Patent Application Ser. No. 60/032,646 filed 10 Dec. 1996.

FIELD OF THE INVENTION

The present invention relates to a biologically active serum-derived composition of matter (SDF), having a low molecular weight, being electrically charged at acidic pH and having absorption at 280 nm, to methods for the isolation thereof and to pharmaceutical compositions comprising the same.

BACKGROUND OF THE INVENTION

Normal hemopoiesis is coordinated by a variety of regulators which include glycoprotein growth factors (cytokines), such as the colony stimulating factors, as well as non-protein small molecules such as the retinoids. They regulate the survival (apoptosis), proliferation and differentiation of progenitor and precursor cells and the activation state of mature cells. Both proliferation and differentiation processes are regulated by positive and negative stimuli. In acute leukemia, a block in the cell differentiation leads to a massive accumulation of proliferative, undifferentiated non-functional cells. Recently, these regulators have been used in a wide array of clinical and laboratory applications. For example, cytokines are used for treatment of patients with aplastic states such as post bone marrow (BM) transplantation, radio-chemotherapy etc., as well as for ex vivo expansion of specific subsets of cells valuable in cell therapy (transplantation, immuno- or gene-therapy). Low molecular weight compounds, such as retinoids, have been used for induction of differentiation in leukemic cells as a therapeutic modality.

The current approach to treatment of leukemia is based on killing the malignant cells by chemo- or radiotherapy. Such treatment is not specific to the malignant cells and damages also dividing normal cells. Therefore, an alternative approach is being developed, based on inducing the undifferentiated leukemic cells to undergo differentiation. Evidently, terminal differentiation of hemopoietic cells is associated with loss of leukemogenicity.

It has been shown that some undifferentiated myeloid leukemia cells respond to cytokines (e.g. IL-6) and undergo differentiation into mature, functional, non-dividing granulocytes or macrophages, and thereby lose their leukemogenic potential [Fibach, E., et al., Nature, New Biology 237:276 (1972); Shabo, Y., et al., Blood 78:2070 (1988); Fibach, E., et al., Proc. Natl. Acad. Sci. USA 70:343–346 (1973); Inbar, M., et al., Proc. Natl. Acad. Sci. USA 70:2577–2581 (1973); Fibach, E. & Sachs, L. J., Cell Physiol. 83:177–185 (1974); Hayashi, M., et al., Int. J. Cancer 14: 40–48 (1974); Fibach, E. & Sachs, L. J., Cell Physiol. 86:221–230 (1975); Fibach. E. & Sachs, L. J., Cell Physiol. 89:259–266 (1975)].

Other differentiation inducers include dimethylsulfoxide, hexamethylene bis-acetamide, butyric acid [Collins, S. J., et al., Proc. Natl. Acad. Sci. USA 75:2458 (1978)], derivatives of vitamins A and D3 [Breitman, T. T., et al., Proc. Natl. Acad. Sci. USA 77:2936 (1980)] and low doses of cytotoxic drugs such as actinomycin D and cytosine arabinoside [Breitman, T. T., et al., ibid.]. Retinoic acid has been used in the treatment of acute promyelocytic leukemia [Chomienne, C., FASEB 10: 1025 (1996)].

Although capable of inducing some cell lines, these inducers have only rarely been found to induce terminal differentiation in cells freshly isolated from leukemic patients [Breitman et al., (1980) ibid.].

Several publications describe some activities of the high molecular weight, copper binding protein, ceruloplasmin (CP) in malignant and aplastic states.

For example, in JP 56120622 and JP 56090015, CP is described as the active ingredient in an antitumor preparation against leukemia. JP 56120622 describes the CP as having a therapeutic activity against several mammalian tumors due to its inhibitory effect on aggravation of cancer. In addition, CP is described as being capable of inactivating the strong oxidative super-oxide anion radicals by converting them into oxygen molecules. It is also mentioned that CP has an effect on the promotion of liver catalase biosynthesis.

JP56090015 describes a preventative and remedial drug for side reactions of anti-malignant tumor agents, which contains human CP as the main ingredient.

JP 56002916 also describes CP as an anti-tumor agent. This publication is concerned with compositions for the prevention and treatment of radiation damages which contain CP as the active ingredient. Animals irradiated with γ-rays, after pre-incubation with a composition comprising CP, showed a high survival rate. The preventive activity described in this publication was specifically attributed to CP.

JP 60149529 relates to the production of differentiation-inducing factors, as a result of administration of CP to mammals. In addition, medicines for leukemia in which the active ingredients are the differentiation-inducing factors produced after treating mammals with CP are described. As indicated in this publication, the differentiation of leukemic cells obtained by the differentiation-inducing factors is induced via a CP stimulus. Serum obtained from rabbits which repeatedly received CP was capable of inducing differentiation of M1 cells into macrophages. However, CP by itself was incapable of inducing the differentiation. There is no indication as to the identity or nature of the substance obtained by CP stimulus, which causes the induction of differentiation.

The use of CP has been described also for the preparation of other pharmaceutical compositions. For example, GB 1,304,697 describes pharmaceutical compositions comprising CP for use, in particular, against inflammation.

Further, clinical trials have shown that CP may be helpful in therapy of aplastic anemia [Shimizu, M., Transfusion 19(6):742–8 (1979); Arimori, S., Jap. J. Clin. Exper. Med. 43:1897 (1966)].

Contrary to the earlier reports, the present invention reveals that the activities previously ascribed to CP, should be attributed to a small molecular weight composition of matter (SDF), which in serum is preferentially associated with CP (SDF-CP complex). Regardless of the nature of association between SDF and CP, it is clear that CP derived from adult serum is a rich source of the factor. Other sources for SDF are urine and fetal serum. Due to its large molecular weight, intact CP cannot be present in the urine. Thus, it is assumed that the factor present in urine is not associated with the CP molecule, or at least not with the intact molecule.

As will be shown hereafter, SDF, as well as its complex with CP, which are the subject of the present invention, may have many therapeutical uses.

SUMMARY OF THE INVENTION

The present invention relates to a biologically active serum-derived composition of matter (SDF), having a low molecular weight, being electrically charged at acidic pH and having absorption at 280 nm. The molecular weight of SDF, as determined by electron spray is 316.

In a second aspect, the invention relates to a method for the isolation from plasma and purification of a low molecular weight composition of matter, comprising the steps of (a) transferring plasma through an affinity column to obtain an electrophoretically homogeneous fraction being the SDF-CP complex, which may be optionally concentrated by transferring through an anion exchange column; (b) isolating the SDF from the SDF-CP complex by either (i) transferring the fraction obtained in step (a) through RP-HPLC "Resource"™ column, elution buffer A consisting of 0.05–0.1% trifluoroacetic acid (TFA) in water (pH 2.5), elution buffer B consisting of acetonitrile, the fractions eluted at acetonitrile concentration of 0–2% and 13–17% being collected and combined, or (ii) extracting the fraction obtained in step (a) with an acidified solvent, wherein the active fraction is recovered from the organic phase; (c) purifying the fraction obtained in (b) by RP-HPLC chromatography separation using a C-18 column, wherein in a first optional separation step elution buffer A, consisting of 0.1% TFA in water (pH 2.5), and elution buffer B, consisting of 0.1% TFA in acetonitrile, are employed, the fraction eluted at acetonitrile concentration of 0–2% being collected, and in the subsequent separation step, elution buffer A, consisting of 0.1% triethylamine in water and adjusted to pH 7.0, and elution buffer B, consisting of acetonitrile, are employed, the fraction eluted at acetonitrile concentration of 9–11% being collected.

Also within the scope of the invention is a biologically active complex comprising ceruloplasmin and said biologically active composition of matter (SDF).

In a second aspect, the invention relates to pharmaceutical composition comprising as active ingredient the SDF of the invention or its complex with CP, and optionally further comprising pharmaceutically acceptable additives.

Such pharmaceutical compositions may be used for treatment of patients with aplastic marrow, for inducing or maintaining remission of tumors, for expanding hematopoietic normal stem and progenitor cells for bone marrow transplants or for inhibiting enhanced angiogenesis.

A: Fragmentation at cone voltage—30 V.
  B: Fragmentation at cone voltage—45 V.
  C: Fragmentation at cone voltage—60 V.

Figure 9A:
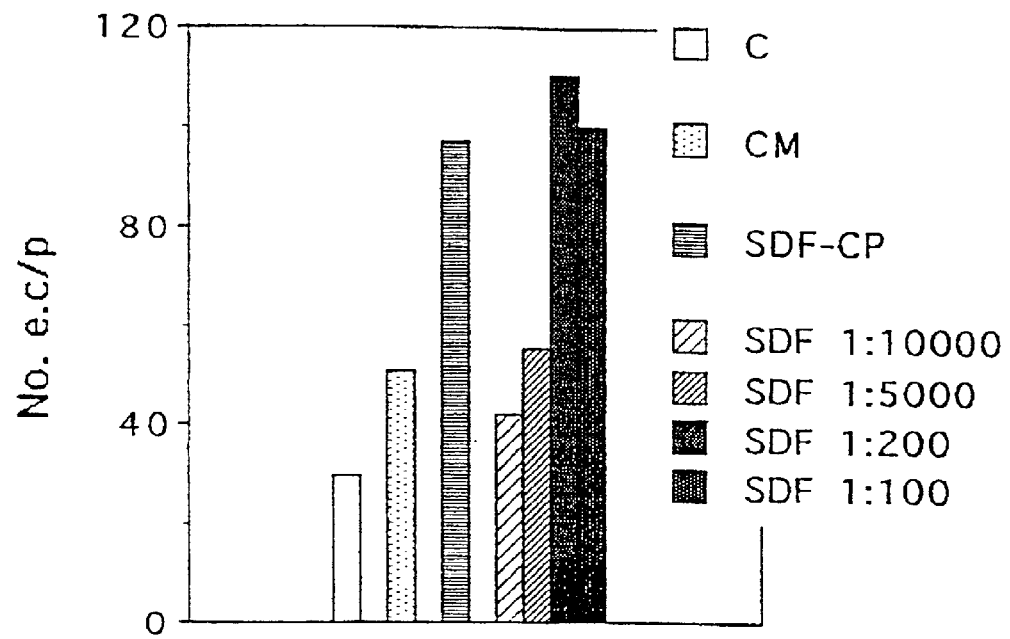
Figure 9B:
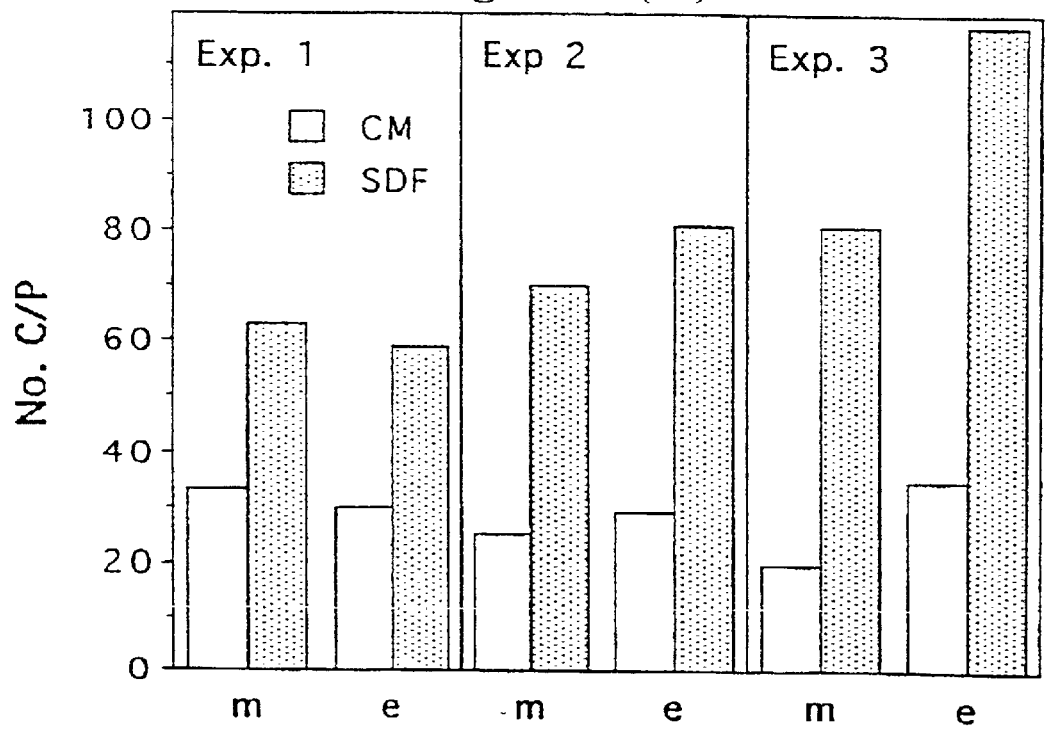

FIG. 9: Effect of SDF on myeloid and erythroid colony growth

A: Light density peripheral blood (PB) cells were cultured in liquid culture (phase 1, as described in the Examples) supplemented with none (C, for control), 5637 CM (10% v/v, (CM)), SDF and SDF-CP complex (SDF-CP) at different dilutions. After 5 days the cells were harvested, washed and cloned in semi-solid medium supplemented with Epo. Colonies were scored on day 14 as illustrated in the figure by the number of erythroid colonies per plate (No. e.c/p).
  B: Light density PB cells were cultured in liquid culture (phase 1) supplemented with 5637 CM (10% v/v, (CM)) or SDF (1:200, (SDF)).

After 5 days the cells were harvested, washed and cloned in semi-solid medium supplemented with 5637 CM for myeloid colonies, or with Epo for erythroid colonies. Colonies were scored on day 14 and is illustrated in the figure by the number of colonies per plate (No. C/P) both for erythroid (e) and for myeloid (m) cells.

Figure 10:
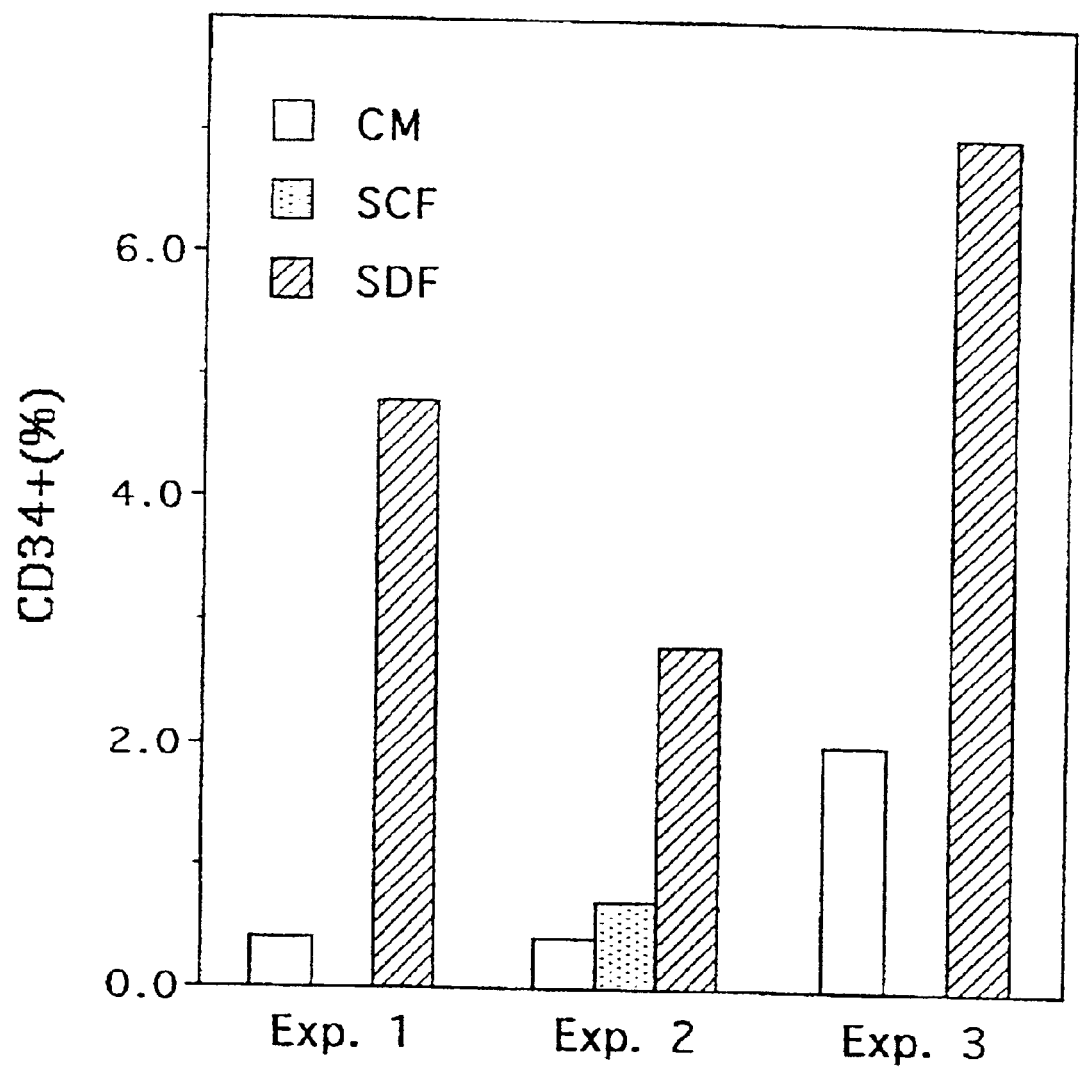

FIG. 10: Effect of SDF on CD34$^+$ cells Light density PB cells were cultured in liquid culture (phase 1) supplemented with 5637 CM (10% v/v(CM)), stem cell factor (SCF) or SDF (SDF). CD34+cells were enumerated by flow cytometry (CD34+ (%)). At the initiation of the culture the percentage of CD34+ cells (CD34+ (%))ranged from 0.1 to 0.5. Three independent experiments are presented (Exp. 1 to Exp. 3). The percent of CD34+ cells was determined in experiment (1) on day 6, in experiment (2) on day 3 and in experiment (3) on day 7.

Figure 11:
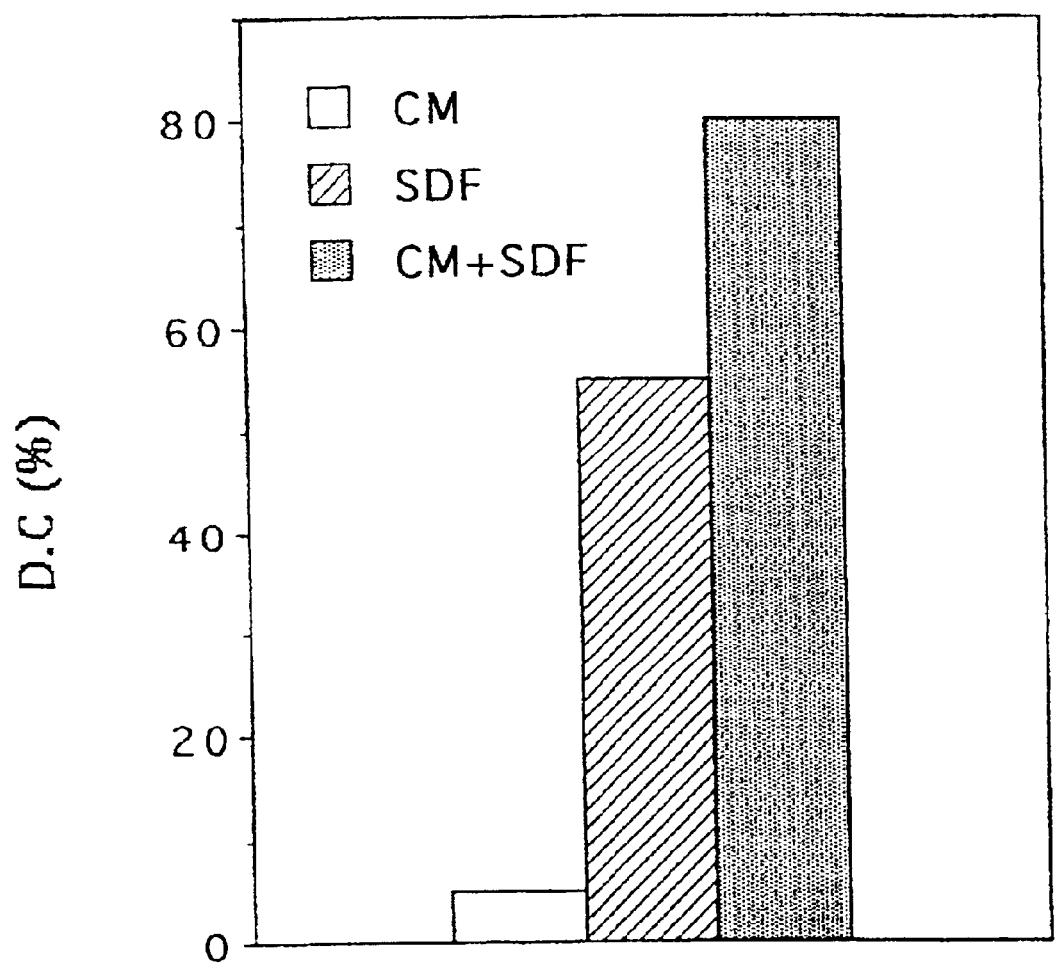

FIG. 11: Effect of SDF on dendritic colony growth Light density PB cells were cultured in liquid culture (phase 1) supplemented with 5637 CM (10% v/v, (CM)), SDF or SDF+5637 CM (SDF+CM). After 3–4 days, the cells were harvested, washed and cloned in semi-solid medium. Dendritic colonies (D.C %) were scored on day 14.

Figure 12:
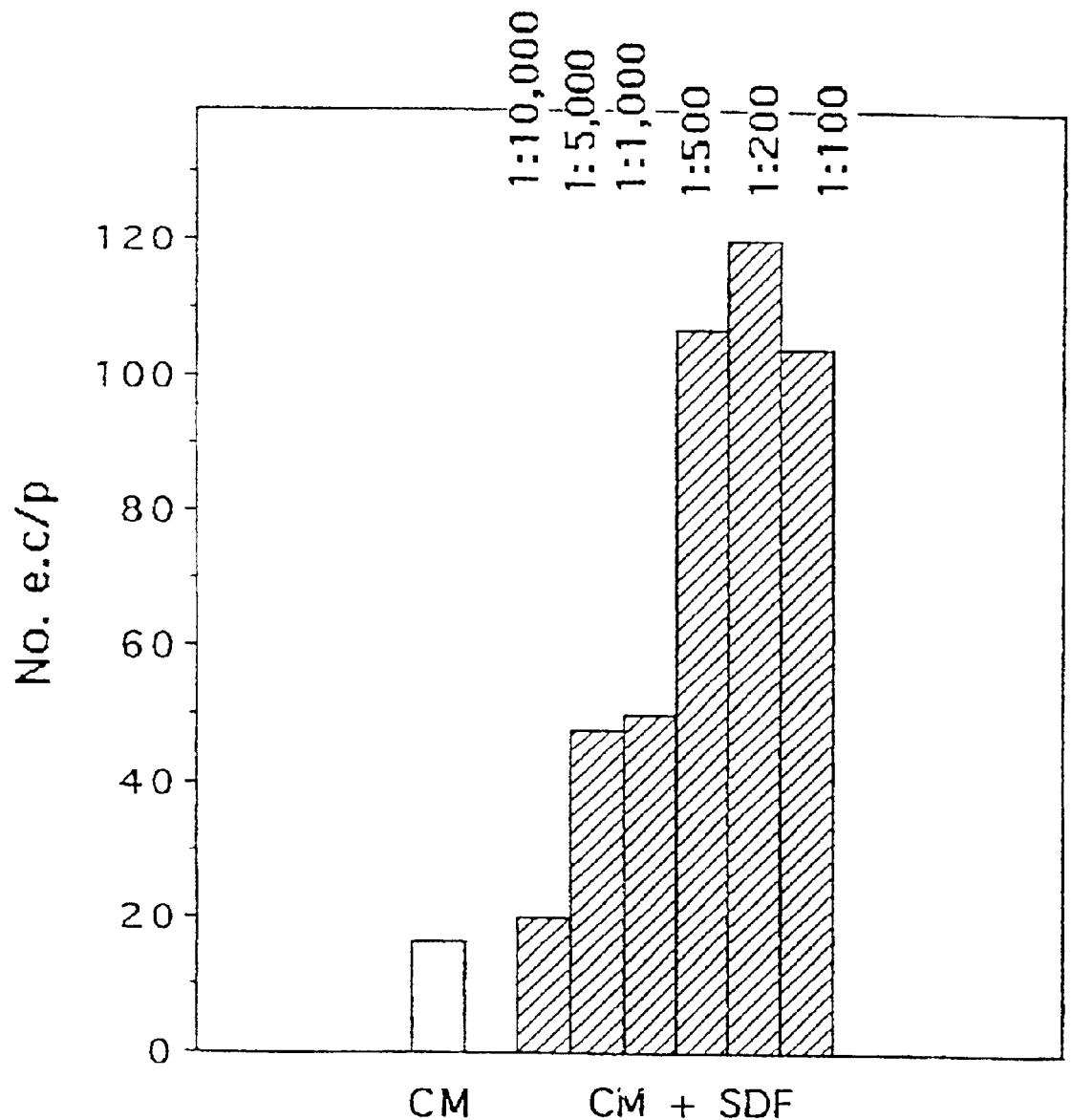

FIG. 12: Effect of SDF on erythroid progenitors derived from pure red cell aplasia Low density PB cells derived form a patient with pure red cell aplasia were cultured in liquid culture (phase 1) supplemented with 5637 CM (10% v/v, (CM)) or SDF+5637 CM (SDF+CM) with the different dilution of SDF indicated in the figure. After 4 days the cells were harvested, washed and cloned in semi-solid medium supplemented with Epo. Colonies were scored on day 14, and is depicted in the figure by the number of erythroid colonies per plate (No. e.c/p).

Figure 13:
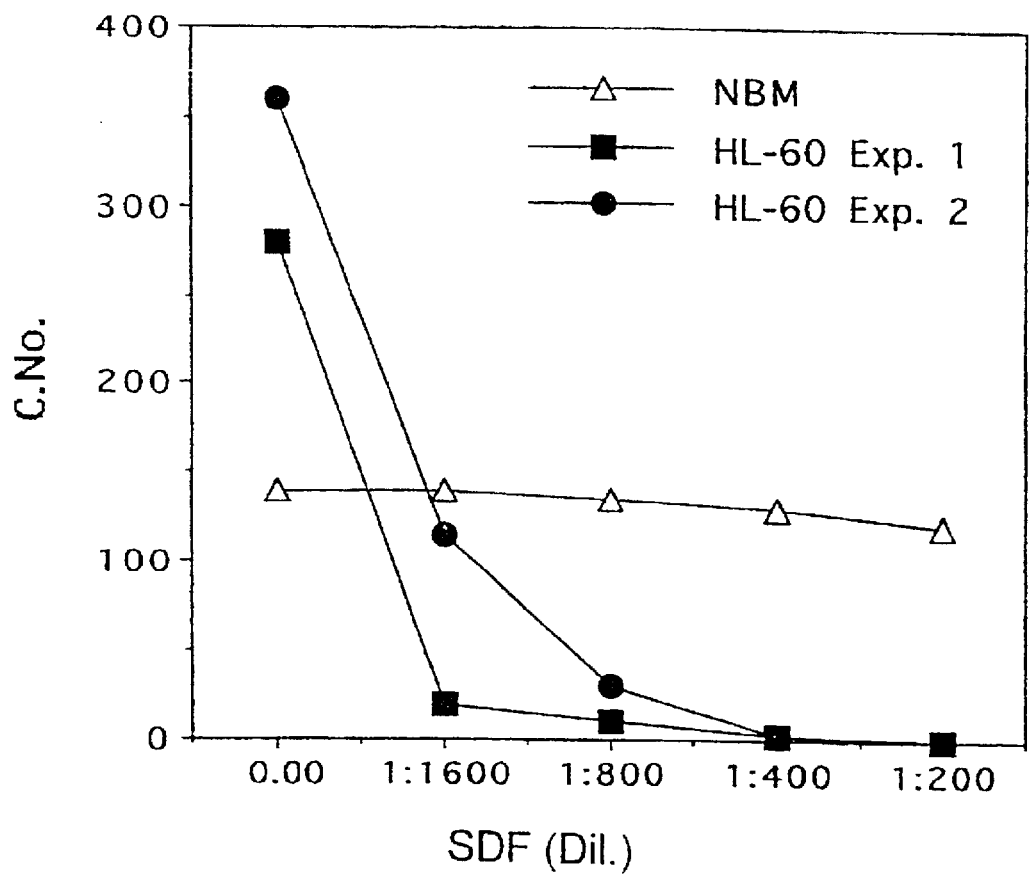

FIG. 13: Effect of SDF on colony formation by leukemic and normal progenitors Leukemic HL-60 cells (HL-60) and normal BM (NBM) progenitors were cloned in agarose cultures stimulated by GM-CSF (100 U/ml) and several dilutions of SDF (SDF(Dil.)). Colonies were scored on day 10. The results are illustrated as colony number as a function of the different SDF dilutions), for HL-60 cells, two sets of experiments (Exp. 1 and Exp. 2) were conducted.

DETAILED DESCRIPTION OF THE INVENTION

The present invention relates to a biologically active serum-derived composition of matter (SDF), having low molecular weight, being electrically charged at acidic pH, and having absorption at 280 nm. The molecular weight of SDF being 316, as determined by electron spray mass spectrometry.

More specifically, SDF is comprised of an aromatic moiety, and carries a double charge, as indicated by the fragmentation thereof on electron spray mass spectrometry.

Figure 2:
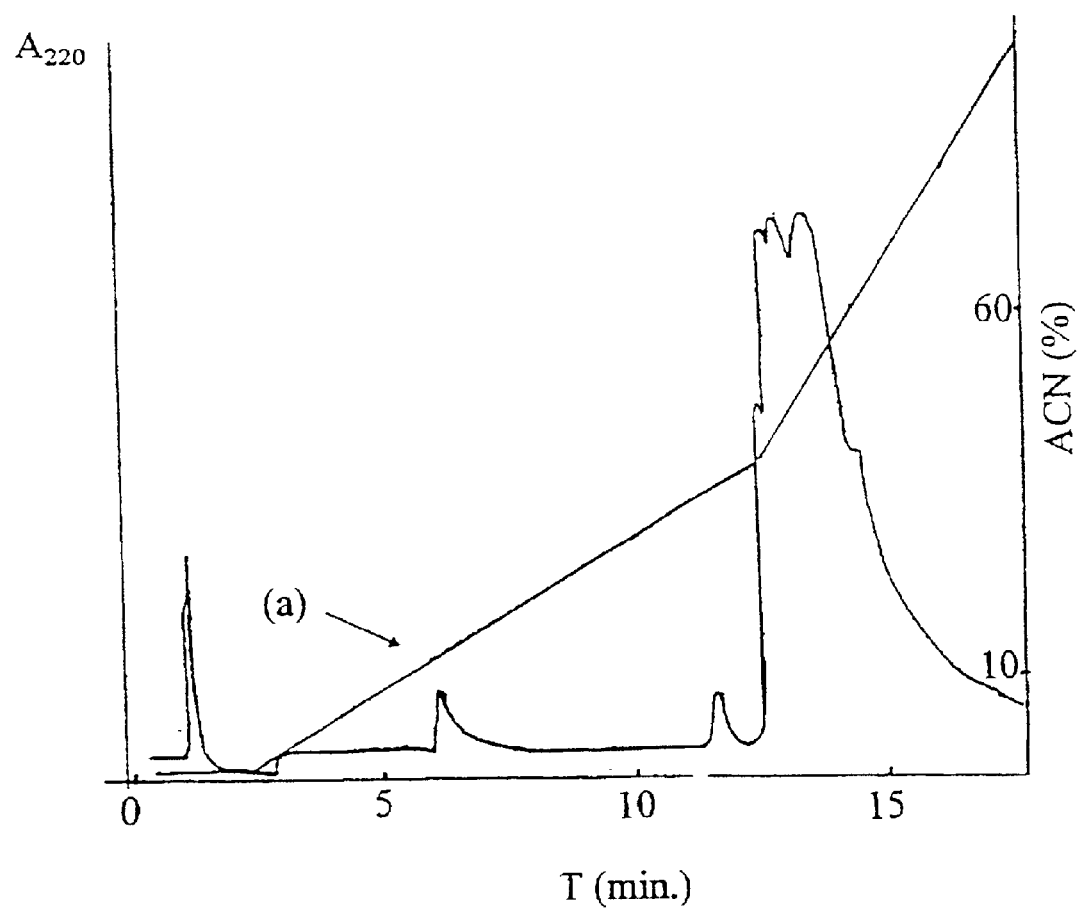
FIG. 2: Separation of SDF from its high MW complex with CP on RP-HPLC 'Resource' column The fraction was separated from its complex and is depicted by the absorbance at 220 nm ($A_{220}$) as function of time (T(min.)). Buffer A—0.1% TFA in $H_2O$ (pH 2.5), buffer B—0.1% TFA in acetonitrile. The gradient is indicated as the acetonitrile percentage in the eluting buffer (ACN(%)), Flow—140 ml/min. SDF fraction is eluted in correlation with the void and after 5–6 min (a).

The invention also relates to a method for the isolation and purification from plasma, of a low molecular weight composition of matter, comprising the steps of:—(a) transferring plasma through an affinity column to give an electrophoretically homogeneous fraction being the SDF-CP complex, which may optionally be concentrated by transferring through an anion exchange column and collecting the bound fraction, having an absorption at 280 nm; (b) isolating the SDF from its complex with the high MW CP protein by either (i) transferring the fraction obtained in step (a) through RP-HPLC "Resource"™ column, elution buffer A, consisting of 0.05–0.1% TFA in water (pH 2.5), and elution buffer B, consisting of acetonitrile, are employed, the active fractions eluted at acetonitrile concentration of 0–2% and 13–17% being collected and combined, said CP fraction being eluted at acetonitrile concentration of about 40% and being devoid of activity; or (ii) extracting the fraction obtained in step (a) with an acidified solvent, wherein the active fraction is recovered from the organic phase whereas CP is recovered from the aqueous phase, in an inactive form. As will be shown hereafter. the two fractions obtained in step (b) were active. The difference in the retention time may be attributed to the state of ionization of the molecule and/or its association with some impurities, probably of small peptides (FIG. 2). The affinity chromatography column employed in step (a) is preferably a tentacle-agarose gel, derived using a reaction of Sepharose CL-6B or Sepharose 4B with chloroethylamine [Calabrese, L., Biochem. Int. 16:199–208 (1988)].

Another purification step is required in order to isolate the SDF from its impurities. The method of the invention thus further comprises (c) purifying the active fraction obtained in step (b) by RP-HPLC chromatography separation, using a C 18 column, wherein in a first optional separation step, elution buffer A, consisting of 0.1% TFA in water (pH 2.5), and elution buffer B, consisting of 0.1% TFA in acetonitrile, are employed, the fraction eluted at acetonitrile concentration of 0–2% being collected (void). This purification step at acidic pH (2.5) results in a partial disassociation of SDF from said impurities. The active fraction is eluted in correlation with the void volume, while most of the impurities are eluted with the gradient. The semi-purified SDF (in case the optional purification at acidic pH is employed) is then subjected to a subsequent separation step, by transferring the same through the same column, employing elution buffer A, consisting of 0.1% triethylamine in water, adjusted to pH 7.0, and elution buffer B, consisting of acetonitrile. The fraction appearing as a single, symmetrical peak, is eluted with acetonitrile concentration of 9–11% and collected. Optionally, the fraction obtained from step (b) is directly separated on the second separation step of (c).

A five-step purification procedure may be employed as an alternative to step (a). This five-step procedure comprises the steps of ammonium sulfate precipitation, anion exchange chromatography (DEAE), cation exchange chromatography (S-Sepharose), dye-ligand (Affigel blue) chromatography and hydrophobic chromatography (TSK-Phenil). Following the last purification step, the purified fraction may be further separated on an SDS-gel.

According to the invention the plasma from which SDF is obtained is human plasma. However, the inventors have found that an active fraction is also present in non-human plasma, in human urine and in bovine fetal serum. Since the full CP protein is too large to be present in the urine, it is assumed that the active fraction present therein is the SDF itself or in association with part of the CP protein or with other small peptides. In view of the above, SDF may be isolated and purified from human or non-human adult or fetal serum or urine, by any suitable method.

The invention also relates to a biologically active complex comprising CP and SDF.

Obviously, any biochemically pure SDF obtained by the method according to the invention are also within the scope of the present invention. The complex of SDF with CP can be obtained, for example, from step (v) of the five-step purification (Example 1B) procedure or after the one step affinity purification procedure of the method of the invention.

As shown in the description hereafter, the present inventors have found that normal serum, which sustains the growth and viability of cells in culture, contains a small molecular weight, natural product that exhibits dual activity on hematopoietic cells: on the one hand, it is extremely potent in stimulating development of a variety of normal blood cells, and, on the other hand, it inhibits leukemic cell growth by inducing terminal differentiation. Since this natural product was purified from serum it was termed "serum-derived factor" (SDF).

Effect of SDF on Normal Hemopoiesis

Use of Hemopoietic Growth Factors in Transplantation

Transplantation of hemopoictic cells, originally obtained from either autologous or allogeneic sources, has become the treatment of choice for a variety of inherited or malignant diseases. Recently, more defined populations, enriched for pluripotent hemopoietic stem cells ($CD34^+$ cells) have been used in such treatments [Van Epps, D. E., et al., Blood Cells 20:411 (1994)]. In addition to bone marrow, stem cells could be derived from other sources, such as peripheral blood and neonatal umbilical cord blood [Emerson, S. G., Blood 87:3082 (1996)]. Compared to autologous bone marrow transplantation, transplantation with peripheral blood cells shortens the period of pancytopenia and reduces the risks of infection and bleeding [Brugger, W., et al., N. Engl. J. Med. 333:283 (1995); Williams, S. F., et al., Blood 87:1687 (1996); Zimmerman, R. M., et al., J. Heamatotherapy 5:247 (1996)]. An additional advantage of using peripheral blood for transplantation is its accessibility. However, the limiting factor in peripheral blood transplantation is the low number of circulating $CD34^+$ cells. Therefore, in order to obtain enough cells for transplantation, peripheral blood derived stem cells are "harvested" by repeated leukophoreses, following their mobilization from the marrow into the circulation after treatment with colony stimulating factors and chemotherapy [Brugger et al. (1995), ibid.; Williams et al. (1996) ibid.].

Preliminary attempts have been made to enrich the $CD34^+$ population by ex vivo expansion in tissue culture containing mixtures of growth factors [Koller, M. R., et al., Blood 82:378 (1993); Lebkowski, J. S., et al., Blood Cells 20:404 (1994)]. Such expansion of functional stem cells from a small number of $CD34^+$ cells may have the following advantages:

It may reduce the volume of blood required for reconstitution of an adult hemopoietic system and may obviate the need for mobilization and leukophoresis [Brugger et al. (1995) ibid.].

It may enable storage of small number of peripheral blood, bone marrow or cord blood $CD34^+$ cells for potential future use of the ex vivo expanded population.

In the case of autologous transplantation in patients with malignancies, decreasing the total volume of blood used and selecting $CD34^+$ cells may reduce the load of tumor cells in the final transplant. Such contaminating tumor cells in autologous infusion can contribute to the recurrence of the disease [Brugger et al. (1995) ibid.].

The cultures may provide a significant depletion of T-lymphocytes, which may be useful in the allogeneic transplant setting for reducing graft-versus-host disease.

Clinical studies have indicated that transplantation of ex vivo expanded cells derived from a small number of peripheral blood $CD34^+$ cells can restore hemopoiesis in patients treated with high doses of chemotherapeutical agents. Nevertheless, the up to date results do not allow for firm conclusions about the long term in vivo hemopoietic capabilities of such cultured cells [Brugger et al. (1995) ibid.; Williams et al. (1996) ibid.].

For successful transplantation, shortening the duration of the cytopenic phase, as well as long-term engraftment, is crucial. Inclusion of intermediate and late progenitor cells in the transplant could accelerate the production of donor-derived mature cells and shorten the cytopenic phase. It is important that ex vivo expanded cells will include, in addition to stem cells, more differentiated progenitors in order to optimize short-term recovery and long term restoration of hemopoiesis. For this purpose, expansion of intermediate and late progenitor cells, especially those committed to the neutrophilic and megakaryocytic lineages, concomitant with expansion of stem cells, is required [Sandstrom, C. E., et al., Blood 6:958 (1995)].

Regarding the autologous transplantation in patients with malignancies, it should be noted that different growth factors, e.g. G-CSF and GM-CSF, are currently used in BM transplantation. They have been shown to shorten the time of neutrophil recovery after transplantation (and chemotherapy), by stimulating myeloid progenitors. However, since myeloid leukemic cells have receptors for these factors, the proliferation of residual malignant cells is also stimulated. Since SDF itself, or its complex with CP, alone, or in combination with GM-CSF, potentiates the proliferation of normal progenitors, but inhibit "spontaneous" and GM-CSF stimulated proliferation of myeloid leukemic cells (Examples 2 to 6), it may have a dual effect: eradication of leukemic cells concomitantly with stimulation of the normal ones.

As exemplified hereafter, leukemic cells, treated with SDF lose their proliferation ability which indicates the cells have lost their leukemogenic potential. Therefore, it is believed that SDF may be of great therapeutical value.

Further, SDF or its complex with CP, is capable of stimulating proliferation of early, normal progenitor cells. Therefore SDF or its complex with CP may be used for ex vivo expansion of normal hematopoietic cells such as stem cells ($CD34^+$) and myeloid and erythroid-committed progenitors as well as antigen-presenting dendritic cells, for BM transplantation treatment, or be utilized, for ex-vivo expansion of specific sub-populations that should be valuable in cell therapy (transplantation and immuno- or gene therapy). In addition SDF or its complex with CP can be applied in vivo, where they may support the recovery of the hemopoietic tissue in aplastic states such as in aplastic anemia or following radio/chemotherapy.

In addition, although effective in inducing differentiation and inhibiting proliferation of leukemic cells, it was found by the inventors that neither SDF nor its complex with CP inhibit normal myeloid or erythroid development. Moreover, SDF or its complex with CP, alone or in combination with other growth or proliferation factors, was found to stimulate the proliferation of normal early progenitor cells. For example:

(a) In vitro stimulation of early hemopoietic stem and committed progenitor cells. SDF was found to stimulate the amplification of early stem ($CD34^+$) cells derived from PB or BM and therefore may be applied for ex-vivo expansion of pluripotent stem cells as well as lineage (granulocytic, erythroid and mega-karyocytic) committed progenitor cells. In combination with late growth factors (added to phase 2, described hereafter in the Examples) SDF increases the number of myeloid and erythroid colony forming cells. Such cultures are important in transplantation of $CD34^+$ enriched populations derived from (immobilized) PB and neonatal cord blood and in gene therapy.

(b) In vivo stimulation of early stem and committed progenitor cells. SDF was found to stimulate in vitro proliferation of progenitor cells derived from the PB of patients with pure red cell aplasia. These results suggest that SDF or its complex with CP be administered, for recovery of normal hemopoiesis, to patients with aplastic states, such as aplastic anemia, Fanconi's anemia, myelodysplastic syndrome or following myeloablative radio/chemotherapy and BM transplantation.

(c) Ex vivo expansion of specific populations of subsets of lympho-hematopoietic cells with therapeutic potential such as the antigen presenting dendritic cells. Dendritic cells are "professional", immunostimulatory, antigen-presenting cells. Various studies have suggested the potential use of dendritic cells in immunotherapy. This modality involves infusion of dendritic cells pulsed in vitro with tumor antigens as therapeutic vaccines, as well as using dendritic cells for priming tumor antigen specific T cells in vitro for use in adoptive T cell therapy [Bernhard, H., et al., Cancer Res. 55:1099 (1995); Protti, M. P., et al., Cancer Res. 56:1210, (1996)]. According to the literature, the best "cocktail" for growing such cells is a mixture of cytokines (GM-CSF, SCF, IL-4, TNFα). When BM cells were cloned in the presence of such a cocktail, 40% of the total number of the developed colonies, contained dendritic cells [Moore, M. A., et al., J. Exp. Med. 182:1111 (1995)]. In order to obtain such colonies from PB progenitors, the cultured population should be enriched for $CD34^+$ cells. SDF or its complex with CP induce commitment/expansion of PB CFU-dendritic. Using SDF or its complex with CP (without TNF or SCF), up to 80% dendritic colonies were obtained from non-enriched PB mononuclear cells.

As will be shown in Example 5, SDF has a potent inhibitory activity on the proliferation of endothelial cells from bovine aorta.

As mentioned above, in addition to BM transplantation, ex vivo expansion of hematopoietic stem cells using SDF or its complex with CP, may be used in gene therapy.

Effect of SDF on Leukemic Hemopoiesis

In addition, SDF or its complex with CP, whether obtained by the method of the invention or by any other suitable method, or synthesized by any suitable procedure, possess several therapeutical activities such as inducing differentiation and inhibiting proliferation of both human and murine established leukemic cell lines and of freshly explanted cells from acute and chronic human myeloid leukemias. In addition, SDF itself or its complex with CP are capable of inducing terminal cell differentiation of leukemic cells. Blast cells lose their leukemic phenotype and turn into functional, non-dividing macrophages. Further, either as a result of said terminal cell differentiation or independent therefrom, said leukemic cells, in the presence of SDF or its complex with CP, lose their ability to proliferate and their ability for self cell renewal. The effect of SDF, or its complex with CP, on leukemic cells makes it potentially useful in the treatment of myeloid leukemias in three clinical settings: (a) for induction of remission, optionally, in combination with other hemopoietic factors or low-dose chemotherapy, using "differentiation-inducing therapy" as the main modality; (b) for maintenance of remission state of tumors and (c) in autologous transplantation, for either in vitro or in vivo purging of residual leukemic cells.

In a different aspect, SDF or its complex with CP, may be utilized for regulating the proliferation and differentiation of hemopoietic cells, by modulating nuclear transcription factors.

Modulating the level of expression of specific genes is a prerequisite for controlling cellular growth and differentiation. Gene expression is controlled by sequence-specific DNA binding proteins (transcription factors) which in certain cases are targets for signal transduction from cell surface receptors. The importance of this process for growth control is emphasized by the finding that several proto-oncogenes, including c-Myc, c-Myb, c-Fos, c-Jun, etc. encode sequence-specific transcription factors [Xanthoudakis, S., EMBO J 11:3323 (1992); Ammendola, R., Eur. J. Biochem. 225:483 (1994)]. Although the activity of these factors can be modulated by phosphorylation, recent evidence has emerged for an additional form of regulation of DNA binding activity which is mediated by changes in reduction-oxidation (redox) status. It is suggested that redox status could provide a general mechanism for post-translational control of transcription factors in an analogous fashion to phosphorylation [Xanthoudakis (1992) ibid.; Ammendola (1994) ibid.]. For example, the binding of Fos-Jun hetero-dimers and Jun-Jun homo-dimers to DNA requires that these proteins be in a reduced state. This form of redox regulation may be widespread because the DNA binding activities of several other transcription factors, including Myb, Rel, and NF-kB are sensitive to changes in their oxidation state in a similar manner.

Recent disclosures suggest the contribution of small redox-potential molecules such as glutathion or large proteins such as thioredoxin [Walker, L. J., Mol. Cell. Biol. 13:5370 (1993)] to the regulation of DNA binding ability of several nuclear transcription factors like Sp-1. In human fibroblast cultures it was shown that small molecules with redox potential like pyrroloquinoline quinone (PQQ) stimulate proliferation [Naito, Y., Life Sciences 52:1909 (1993)]. The potency of PQQ was shown to be comparable to that of epidermal growth factor and is much higher than that of fibroblast growth factor or insulin growth factor. Pyrrolidine derivatives of dithiocarbamates trigger myeloid differentiation through AP-1 regulation [Aragones, J., J. Biol. Chem. 271:10924 (1996)]. Therefore, it may be concluded that small molecules with redox potential activity could modulate cell proliferation and differentiation via the regulation of transcription factors activity.

It was found by the inventors, that PQQ at high concentrations can induce differentiation of leukemic cells and stimulate proliferation of normal cells (Example 6). Nevertheless, in view of the high concentrations required, and compared to SDF, the efficiency of PQQ is low. Nevertheless, since SDF is a low molecular weight composition of matter, believed to be carrying a double negative charge, and in view of its potency in inducing differentiation, it is anticipated that, similarly to PQQ, SDF possesses a redox potential activity and consequently might modulates cell proliferation and differentiation via the regulation of transcription factors activity.

Effect of SDF on Angiogenesis

In a different aspect, SDF was found to have a potent inhibitory activity on endothelial cell proliferation, and therefore it might be applicable for inhibiting angiogenesis In certain pathological conditions angiogenesis is dramatically enhanced and is no longer self-limited. Pathological angiogenesis is seen during the development of many diseases, for example rheumatoid arthritis, psoriasis, retrolental fibroplasia, diabetic retinopathy and hemangiomas, during the rejection of organ transplants and most importantly in solid tumor malignancies. Well vascularized tumors expand both locally and by metastasis, while avascular tumors do not grow beyond a diameter of 1–2 mm. It has been suggested that this is the results of lack of balance between angiogeneic stimulators and inhibitors [Folkman, J., New Engl. J. Med. 285:1182–1186 (1971); Folkman, J., J. Natl. Cancer Inst. 82: 4–6 (1989)].

In another aspect, pharmaceutical composition comprising as active ingredient SDF or its complex with CP and optionally further comprising pharmaceutically acceptable additives are within the scope of the invention. Such pharmaceutical compositions may be used for inhibiting enhanced angiogenesis in diseases where uncontrolled angiogenesis is associated with the pathological manifestations.

Other pharmaceutical composition of the invention may be for inducing remission of tumors comprising as active ingredient the SDF of the invention, and optionally further comprising pharmaceutically acceptable additives.

Alternatively, the pharmaceutical composition of the invention can be used for maintaining tumor remission state comprising as active ingredient the SDF of the invention, and optionally further comprising pharmaceutically acceptable additives.

Further, pharmaceutical composition for expanding hematopoietic normal stem and progenitor bone marrow transplants comprising as active ingredient SDF, and optionally further comprising pharmaceutically acceptable additives are also with in the scope of the invention.

The magnitude of therapeutic dose of the SDF on the invention will of course vary with the group of patients (age, sex etc.), the nature of the condition to be treated and with the route administration and will be determined by the attending physician.

The pharmaceutical composition of the invention can be prepared in dosage units forms. The dosage forms may also include sustained release devices. The compositions may be prepared by any of the methods well-known in the art of pharmacy.

In the pharmaceutical compositions of the pharmaceutically acceptable additives may be any pharmaceutical acceptable carrier, excipient or stabilizer, and optionally other therapeutic constituents. Naturally, the acceptable carriers, excipients or stabilizers are non-toxic to recipients at the dosages and concentrations employed.

Finally, within the scope of the invention, is the use of SDF or its complex with CP, in the preparation of a variety of pharmaceutical compositions.

EXAMPLES

Example 1

Separation and Purification of SDF

A: One Step Affinity Purification of the SDF-high MW Complex

In order to separate the CP from the plasma, a human plasma was transferred through an affinity column. The affinity chromatography procedure is based in the tentacle-agarose gel procedure [Robert, V. S., Biochemistry International 27:281–289 (1992)], which preferentially binds the CP protein. The gel was derived by reacting Sepharose CL-6B or Sepharose 4B with chloroethylamine [Robert (1992) ibid.].

Figure 1:
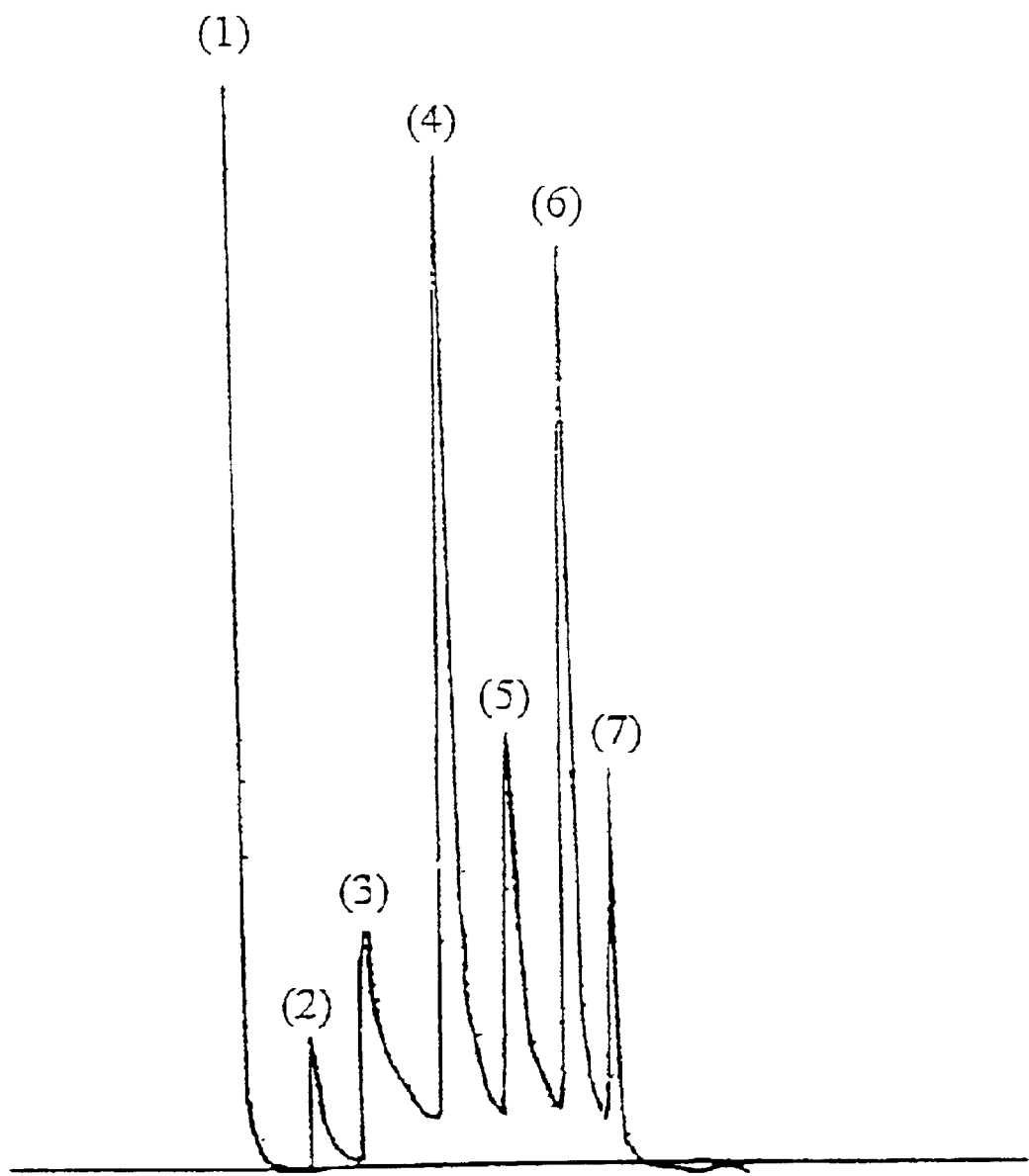
FIG. 1: Affinity purification of the SDF-CP complex from plasma The fraction obtained following precipitation of plasma with 30–60% ammonium sulfate was equilibrated in 10 mM tris buffer, pH 7.4, conductivity –5 mS, and separated on tentacle agarose gel (200 ml bed volume equilibrated in the same buffer). Stepwise elution was performed with 0.1, 0.2, 0.3, 0.5, 1.0 M NaCl in tris buffer and the eluates were analyzed for activity. SDF activity was found to be eluted with 0.5 M NaCl (peak 6).

Optionally, prior to transferring the plasma through an affinity column, the plasma may be precipitated by ammonium sulfate, at a cut-off of 30–60%, equilibrated in 10 mM tris buffer pH 7.4, conductivity 5 ms and then separated on a tentacle-agarose gel as described above,. Elution was performed stepwise with: 0.1, 0.2, 0.3, 0.5, 1.0 M NaCl in tris buffer (FIG. 1).

In order to concentrate the electrophoretically homogeneous CP fraction obtained from the affinity chromatography, the fraction was transferred through an anion exchange column (DEAE, or QAE Sephadex columns). The column and the fraction were equilibrated with 300 mM NaCl in tris buffer. The bound fraction was eluted with 300 mM NaCl in tris buffer.

B: Five Step Purification of the SDF-high MW Complex (i) Ammonium sulfate precipitation—Thirty liters of human plasma were centrifuged. To the clear supernatant solid ammonium sulfate was added to a final concentration of 60% and then stirred for 4 hr at room temperature. The slurry mixture obtained was centrifuged, the precipitate discharged. An additional amount of solid ammonium sulfate was added to the supernatant up to 85% saturation. After 24 hrs of stirring, the slurry mixture was centrifuged and the precipitate dissolved in 6 L of tris buffer 10 mM (pH 7.5), 50 mM NaCl, and diafiltered against the same buffer, using 3K cut off membrane. The diafiltration was completed when conductivity reached 5 mS and the volume of the solution reduced to 4 L. The solution obtained was clear, no pellet was seen upon centrifugation at 14000×g for 10 min., 2.4×10 mg of protein were recovered.

(ii) Anion exchange chromatography—The fraction obtained from step (i) was equilibrated with tris buffer 20 mM (pH 7.4), 120 mM NaCl (conductivity 120 mS), and pumped on a DEAE column (Pharmacia LKB Biotechnology AB, Uppsala Sweden, bed volume 1 liter (11.2 d×10 h)), previously equilibrated with the same buffer at flow 2.5 L/hr. The column washed with the loading buffer until the effluent O.D. at 280 nm returned to the base-line. The elution buffer employed was a linear salt gradient from 120 mM NaCl to 500 mM NaCl in tris buffer. The activity was eluted with 300 mM NaCl.

The DEAE-derived fractions were diluted v/v with tris buffer 25 mM (pH 7.4), 100 mM NaCl. n-Butanol was added dropwise while stirring until an upper butanol phase was obtained. After centrifugation the two phases (aqueous and butanolic) were collected separately. The butanolic phase was evaporated and redissolved in ethanol or in the tris buffer and assayed for activity. The aqueous phase was further separated on a DEAE column. The bound protein was step eluted with tris buffer (pH 7.4), 1M NaCl. The activity was recovered from the bound fraction.

(iii) Cation exchange chromatography—The aqueous fraction obtained from the butanol extraction and DEAE step elution was further separated on a S-Sepharose column (Pharmacia, 800 ml bed volume). Elution buffer A consisting of 20 mM acetate buffer (pH 5.0), 40 mM NaCl (conductivity 4 mS), elution buffer B consisting of 20 mM acetate buffer (pH 5.0), 0.6 mM NaCl. The column, equilibrated with buffer A was loaded with fraction. adjusted to the conditions of buffer A. Elution gradient employed was a linear salt gradient, starting from 100% buffer A, to 100% buffer B. The activity was eluted with 300 mM NaCl.

(iv) Dye-ligand (Affigel blue) chromatography—The pooled active fraction obtained from the S-Sepharose chromatography was separated on an affinity Gel Blue column (50–100 mesh, Bio-Rad, Cat. No 153-7301, column bed volume 40 ml). Elution buffer A consisting of 50 mM tris buffer (pH 7.4), 24 mM KCl and 2 mM ZnCl (conductivity 5.5 mS), elution buffer B consisting of 50 mM tris buffer (pH 7.4), 24 mM KCl and buffer C consisting of 50 mM tris buffer (pH 7.4), 1 M KCl, were employed. The column previously equilibrated with buffer A was loaded with the active fraction which was adjusted to the conditions of buffer A and pumped at flow 3 ml/min. The protein was eluted with a step elution employing 100% buffer.

(v) Hydrophobic chromatography—Pooled active fraction obtained from the Affigel blue was further separated on a TSK-phenyl column (Pharmacia, bed volume 15 ml). Elution buffer A consisting of 50 mM tris buffer (pH 7.4), 20% ammonium sulfate, buffer B consisting of 50 mM tris buffer (pH 7.4) and buffer C consisting of 20% ethanol in 50 mM tris buffer (pH 7.4). The column previously equilibrated with buffer A was loaded with the active fraction, adjusted to the conditions of buffer A. Negative salt gradient (ammonium sulfate) was employed, from 100% buffer A to 100% buffer B, followed by a continuous step elution with buffer C. The activity was eluted with 5–10% ammonium sulfate.

The five-step procedure is summarized in Table 1.

In either procedure (A or B), an electophoretically homogeneous fraction of SDF in its complex with CP was obtained (97KD MW), (data not shown). Seventy percent of the SDF activity was recovered from the 97KD band whereas 30% of the activity was recovered from a fraction in correlation with the front of the gel.

TABLE 1

Purification of SDF-complex - Summary

| Purification steps | Protein (mg) | Units × $10^5$ | Specific activity | Purification (fold) | Recovery (%) |
|---|---|---|---|---|---|
| Human plasma (30 liters) | $2.4 \times 10^6$ | — | — | — | — |
| Ammonium sulfate + Ion Exchange chromatography | $4.76 \times 1^3$ | 3 | 63 | 600 | 100 |
| N-butanol extraction + DEAE (step elution) | $1.3 \times 10^3$ | 2.8 | 215 | 2220 | 93 |
| Dialysis (pH 5) | 700 | 2.3 | 329 | 4100 | 82 |
| S-Sepharose | 70 | 1.6 | 2286 | 41000 | 70 |
| Affi-Gel Blue | 10 | 0.8 | 8000 | 287000 | 50 |
| TSK Phenyl | 5 | 0.7 | 14000 | 574000 | 87.5 |

Total purification-480,000 fold
SDF recovery-23%

Following the last purification step, the purified fraction may be separated on an SDS-gel: 70% of the activity was recovered from a protein band that correlates with MW of 97KD while 30% of the activity was recovered from a low MW fraction at the front of the gel. The 97KD band was sequenced and found to correspond to the copper binding protein-ceruloplasmin. The low MW fraction was also sequenced and analyzed by mass spectrum and found to contain several peptides of 1–2 KD MW. In order to separate the SDF molecule from the high MW complex obtained in step (v), the complex was subjected to purification by steps (b) and (c) described above.

SDF Isolation from its High MW Complex with CP

The SDF fraction can be isolated from the complex in two alternative procedures:

A: RP-HPLC "Resource"™ chromatography—The active fraction was separated from 9 mg purified complex on a RP-HPLC column (3 ml, Pharmacia) comprised of polystyrene/divinyl benzene beads. (FIG. 2). Buffer A consisting of 0.1–0.05% TFA in $H_2O$, buffer B consisting of acetonitrile. flow 3 ml/min, absorption at $A_{220}$. Two SDF peaks at 0–2% and 13–17% acetonitrile were detected and collected.

B: solvent extraction—The active fraction was separated from its complex with CP by solvent extraction with an acidified solvent. A mixture of SDF-CP, 1 M HCl and butanol (1:4:10) was shaken and then centrifuged (at about 2000×rpm) for 5 min. The aqueous and organic phases were collected separately. The SDF activity was recovered in the organic phase while the CP fraction was present in the aqueous phase. Methanol, acetonitrile or chloroform may also be used as the solvent.

SDF Purification

RP-HPLC chromatography—Purification of SDF by RP-HPLC separation procedure, employing a C-18 column (Vydac 2.1×280 mm).

Figure 3:
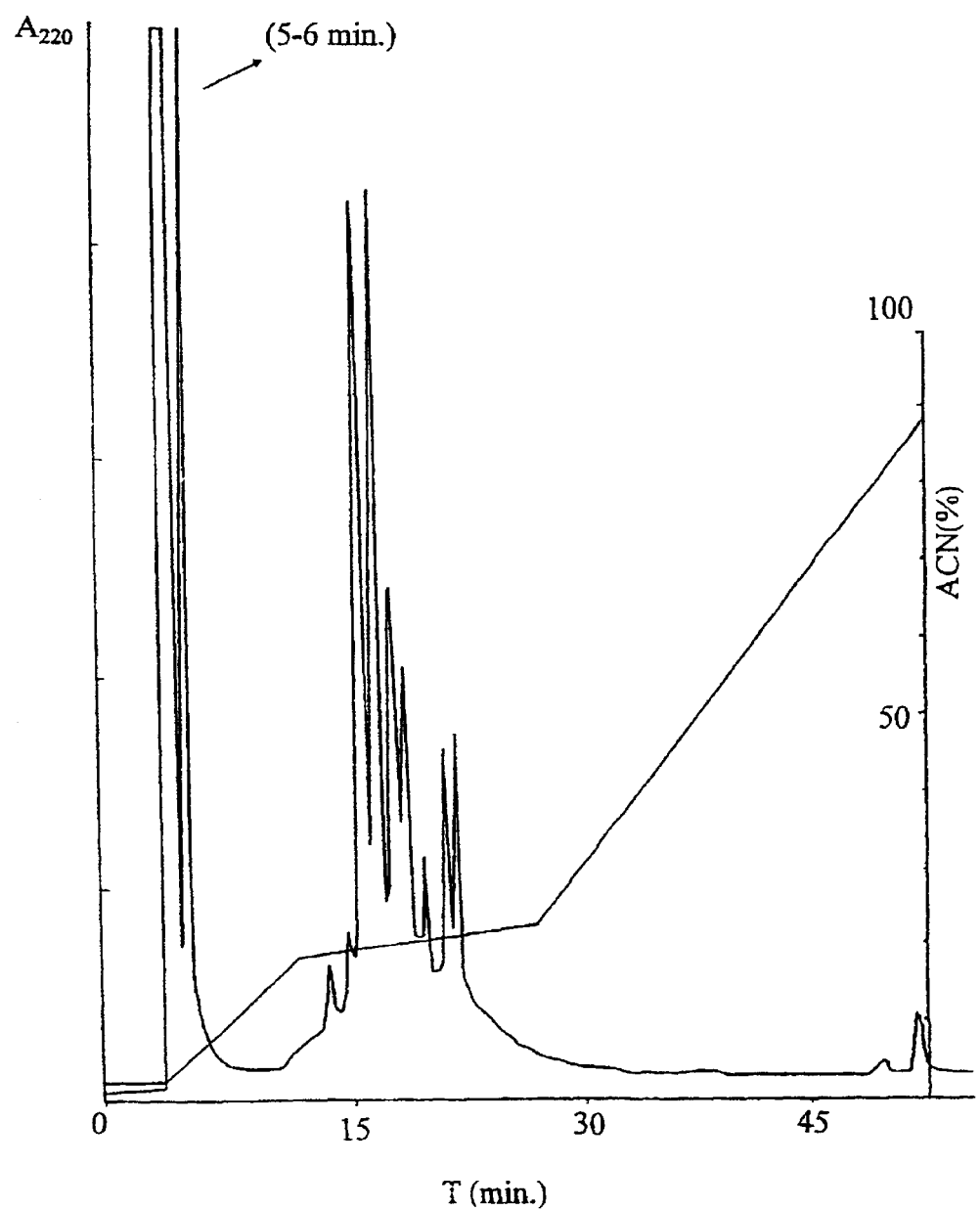
FIG. 3: RP-HPLC separation of SDF from co-eluted contaminants at pH 2.5 Active fractions derived from the resource separation of FIG. 1 were further separated on a C18 (Vydac 2.1×280) RP-HPLC column, which is depicted by the absorbance at 220 nm ($A_{220}$) as a function of time (T(min.)). Buffer A—0.1% TFA in $H_2O$ (pH 2.5), buffer B—0.1% TFA in acetonitrile. The gradient is presented as a function of acetonitrile percentage in the eluting buffer (ACN(%)), Flow—140 ml/min. SDF activity was eluted after 5–6 min.

In a first purification step an elution buffer having a pH of 2.5 was employed. buffer A—0.1 TFA in $H_2O$, and buffer B—0.1% TFA in acetonitrile. The SDF fraction was eluted with about 0–2% acetonitrile, after 5–6 min (FIG. 3), which correlated with the void volume.

Figure 4:
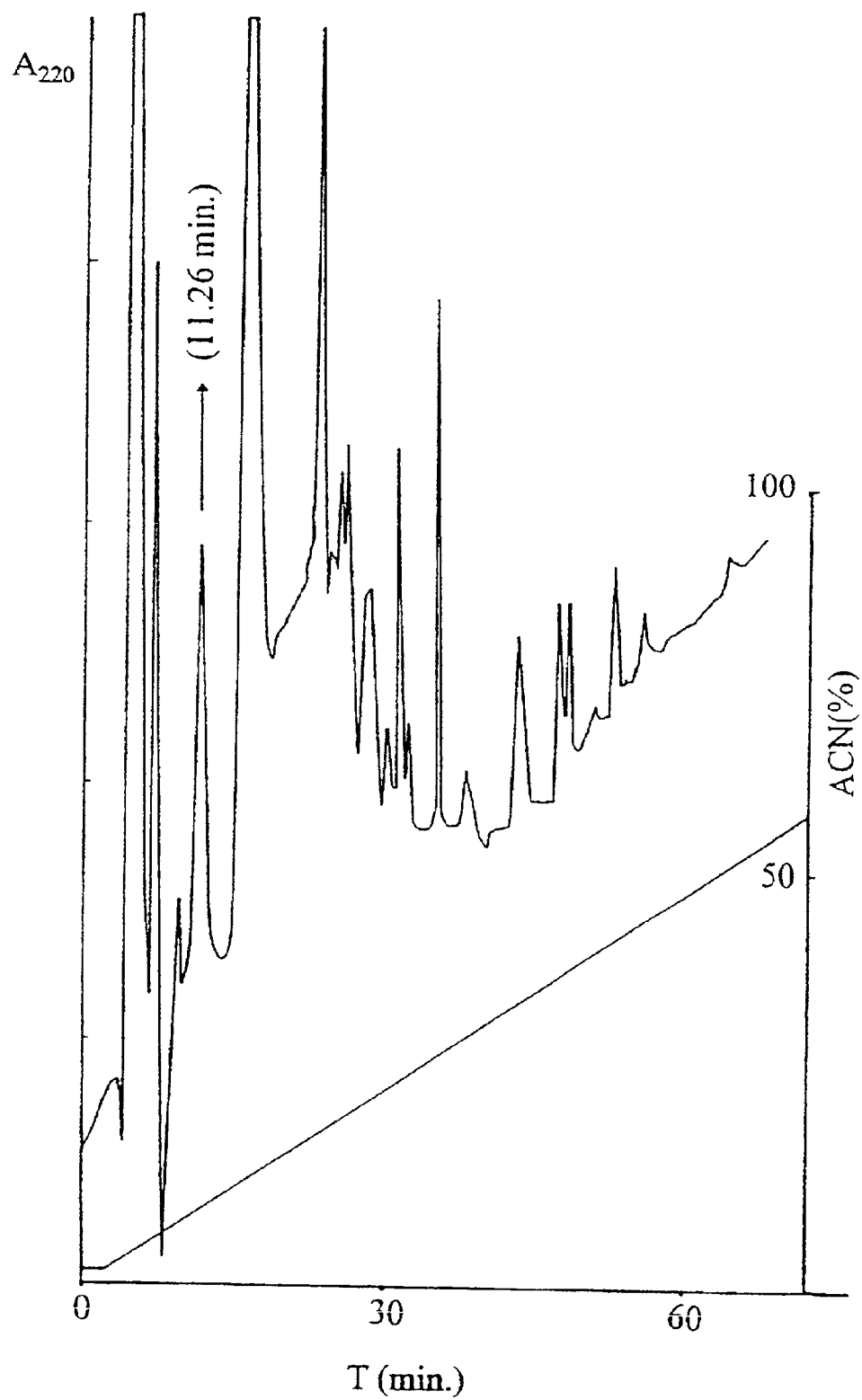
FIG. 4: RP-HPLC separation of SDF from co-eluted contaminants-at pH 7 'Resource' derived fraction at 5–6 min was further separated on C-18 (Vydac 2.1×280) RP-HPLC at pH 7 and is depicted by the absorbance ($A_{220}$) as a function of time (T(min.)). Buffer A: 0.1% triethylamine in $H_2O$ adjusted to pH 7.0 with TFA. Buffer B: acetonitrile. Flow: 140 ml/min. The gradient is illustrated as the acetonitrile percentage in the eluting buffer (ACN(%)). The activity was recovered at 11.26 min. in correlation with a single symmetric peak.

In a second purification step, buffer A consisting of 1% triethylamine in water, adjusted to pH of 7.0 and buffer B consisting of acetonitrile were employed. The SDF fraction was eluted with about 9–11% acetonitrile, after 11–12 min (FIG. 4).

Figure 5:
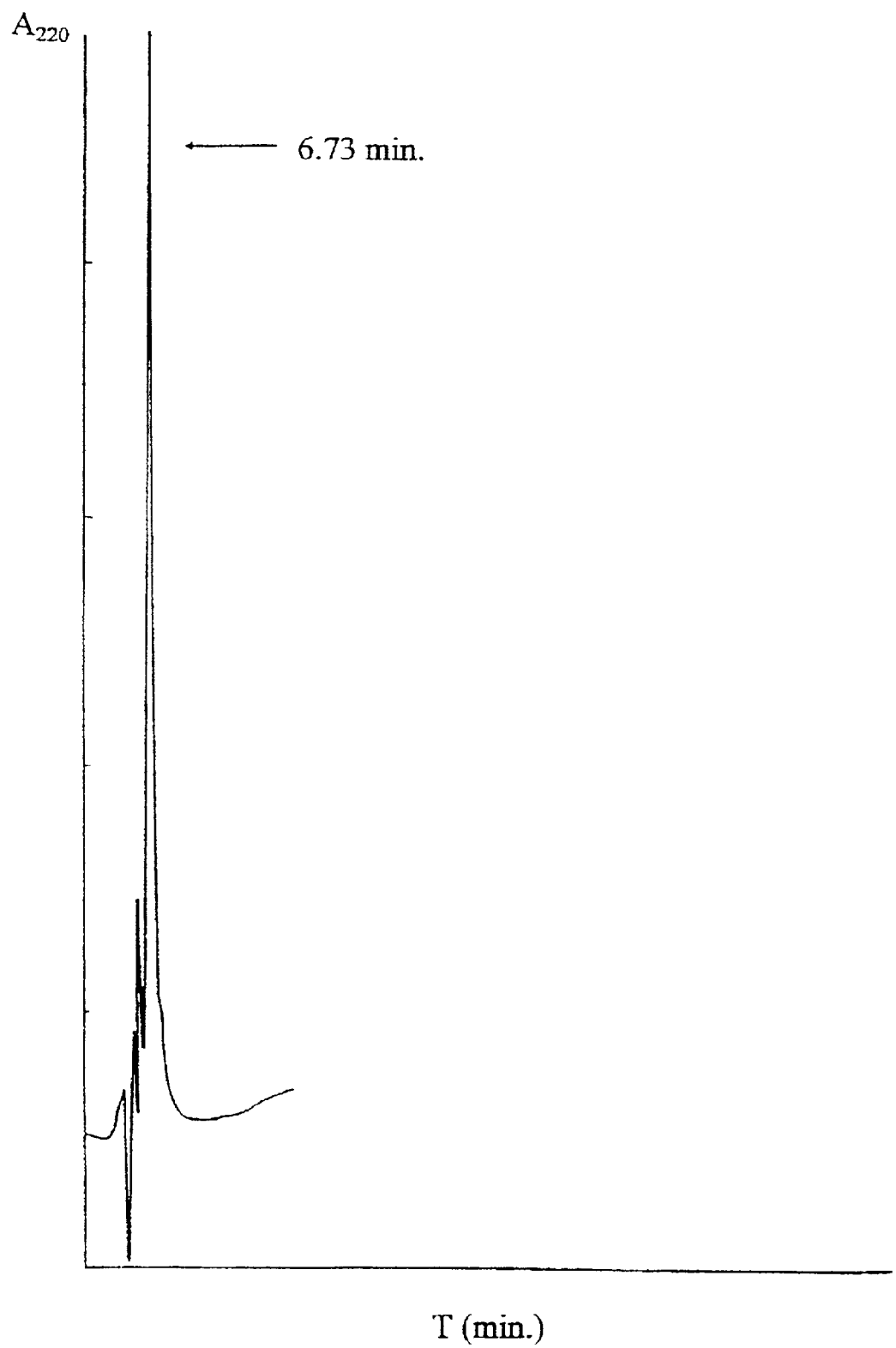
FIG. 5: Purification of SDF on RP-HPLC Active fractions, pooled from the separation on RP-HPLC at pH 7. were re-chromatographed on C-18 at pH 2.5 as depicted in the figure by the absorbance ($A_{220}$) as function of time (T(min.)). The gradient is indicated by the acetonitrile percentage (ACN%) in the eluting buffer. The activity was recovered from the single peak eluted at 6.73 min.

The fractions eluted at 11.26 min, from the second RP-HPLC separation step (FIG. 4), were pooled and rechromatographed with the same conditions as in the first RP-HPLC separation step, only to obtain a single, symmetrical peak at 5–6 min. The purpose of the rechromatography step, is to show that the fraction obtained after the second separation is a single homogenous peak (FIG. 5).

Example 2

Characterization of SDF

Ultraviolet Absorption

Figure 6:
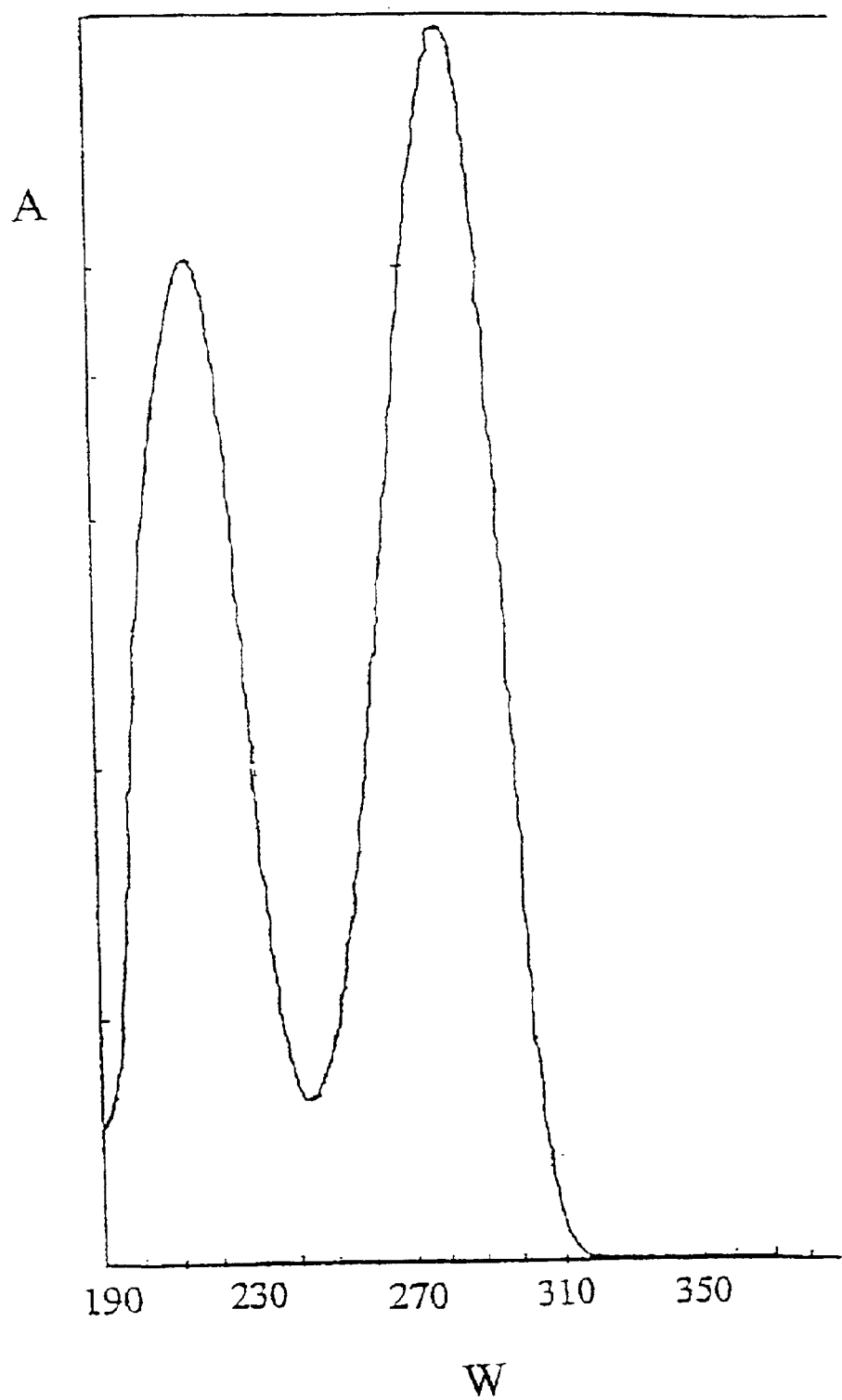
FIG. 6: UV spectrum of purified SDF Purified SDF obtained as described in the following Examples was analysed by UV spectra. The figure illustrates the absorbance (A) as a function of the wavelength (W) in nm.

Ultraviolet absorption spectrum of the active peak eluted from the C-18 column (FIGS. 4–5) suggests the presence of a dominant aromatic compound as indicated by the absorbance at 280 nm (FIG. 6). This fraction was further subjected to amino acid analysis and sequencing, the results of which were both negative. Therefore, it was concluded that the SDF, although purified up to this step in association with peptides, the active compound is most likely not a peptide.

Mass Spectroscopy

Figure 7:
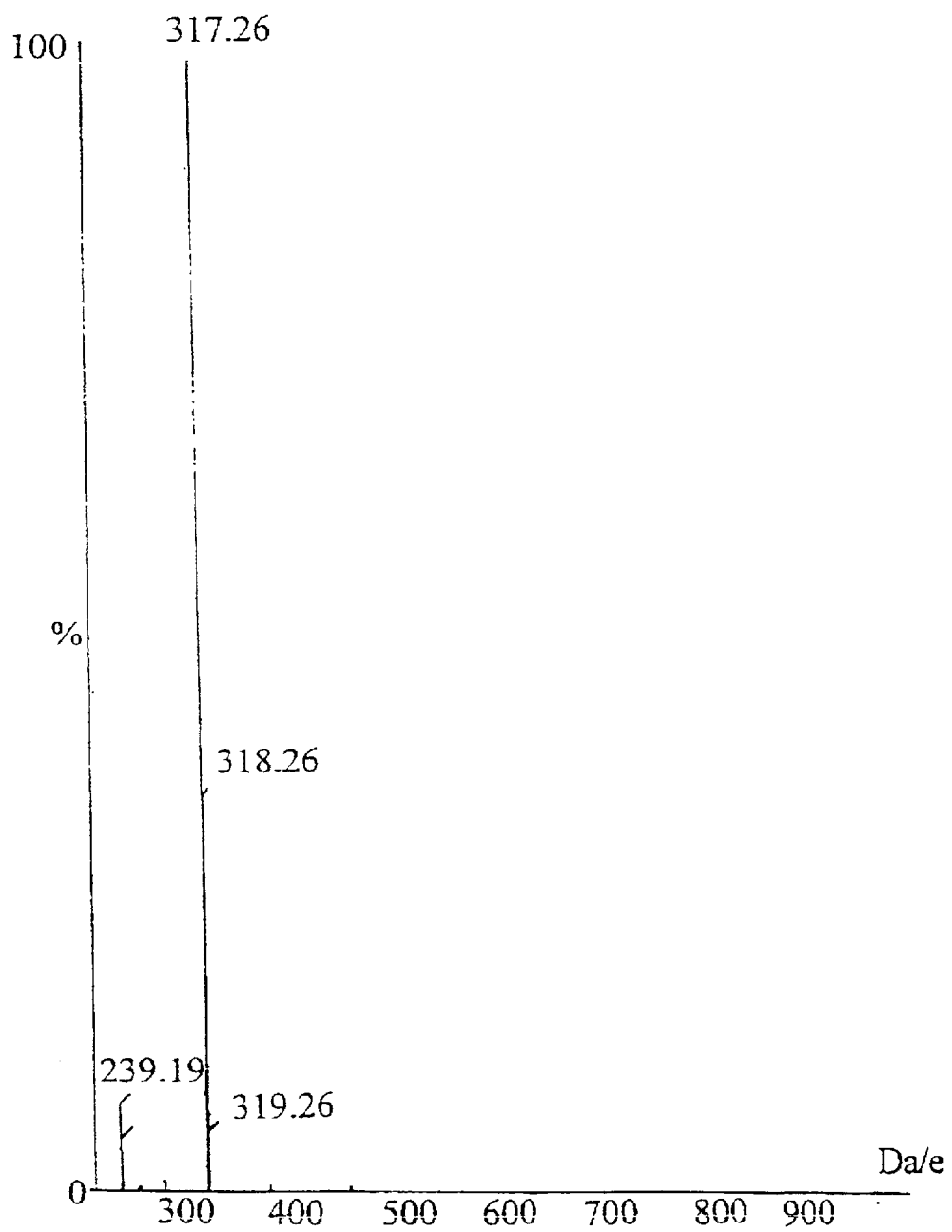
FIG. 7: Mass Spectrum of SDF Purified SDF obtained as described in the following Examples was analysed by mass spectrometry (electron spray).
Figure 8A:
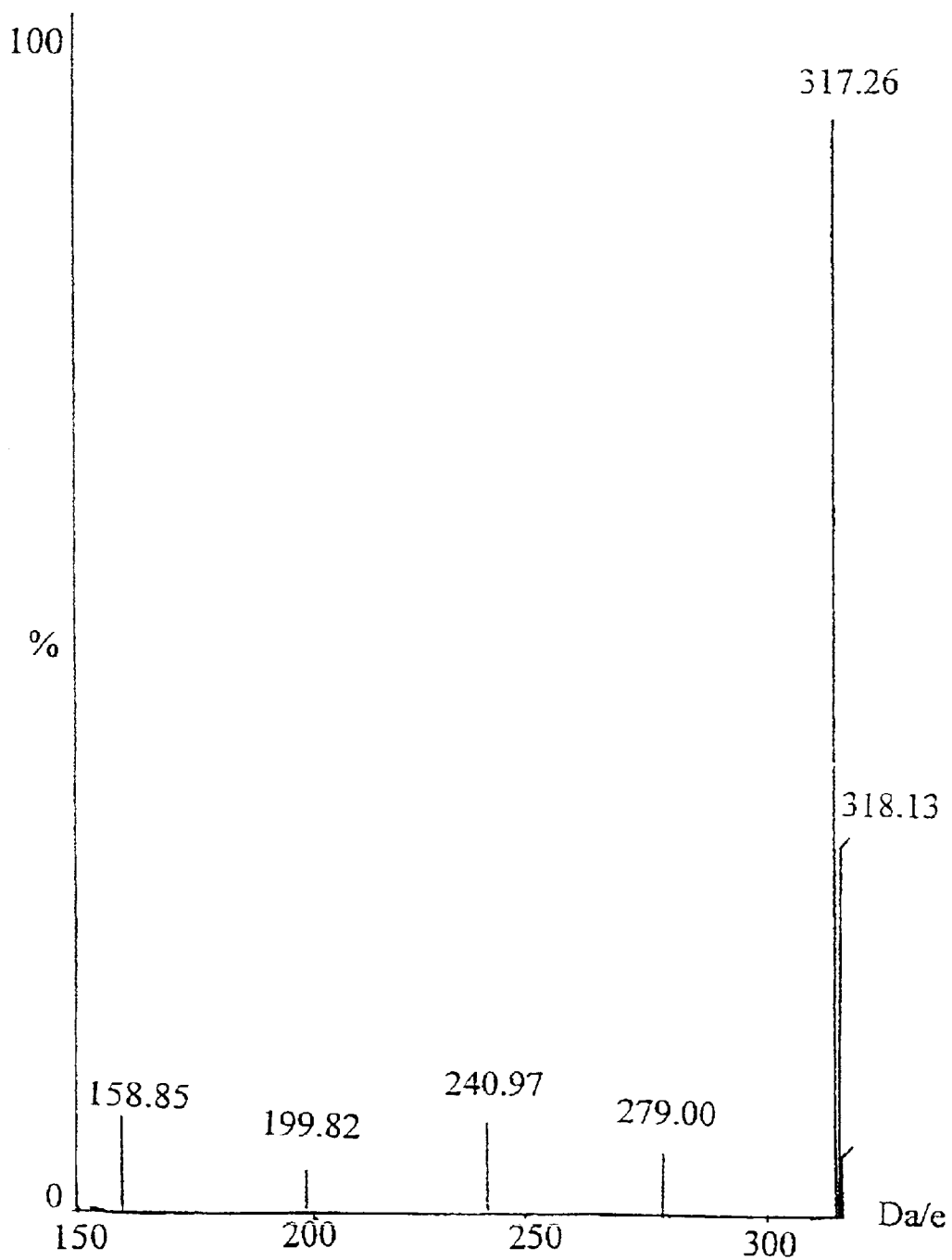
FIG. 8: Fragmentation and analysis of the 316 MW fraction by Mass Spectrometry
Figure 8B:
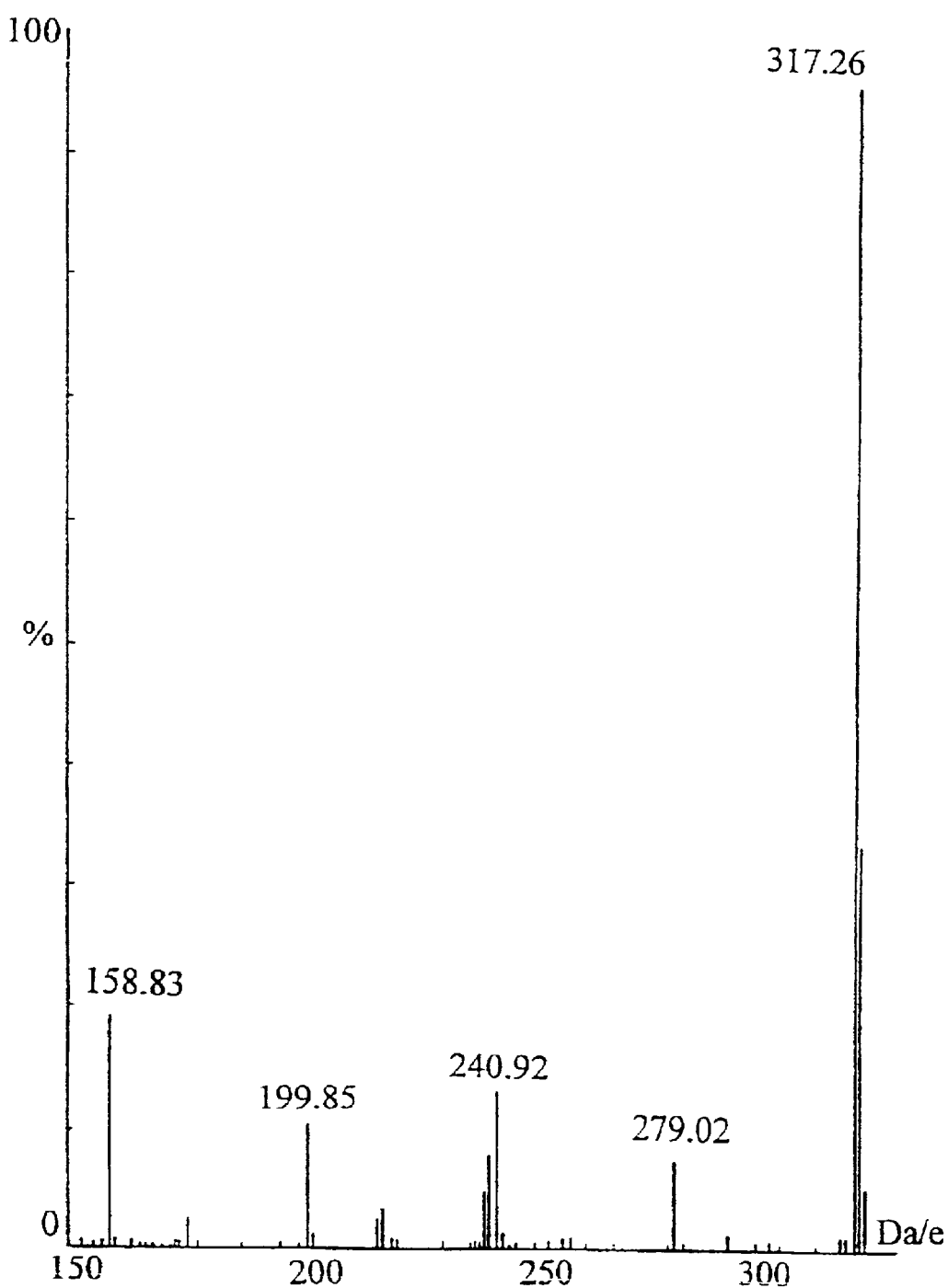
Figure 8C:
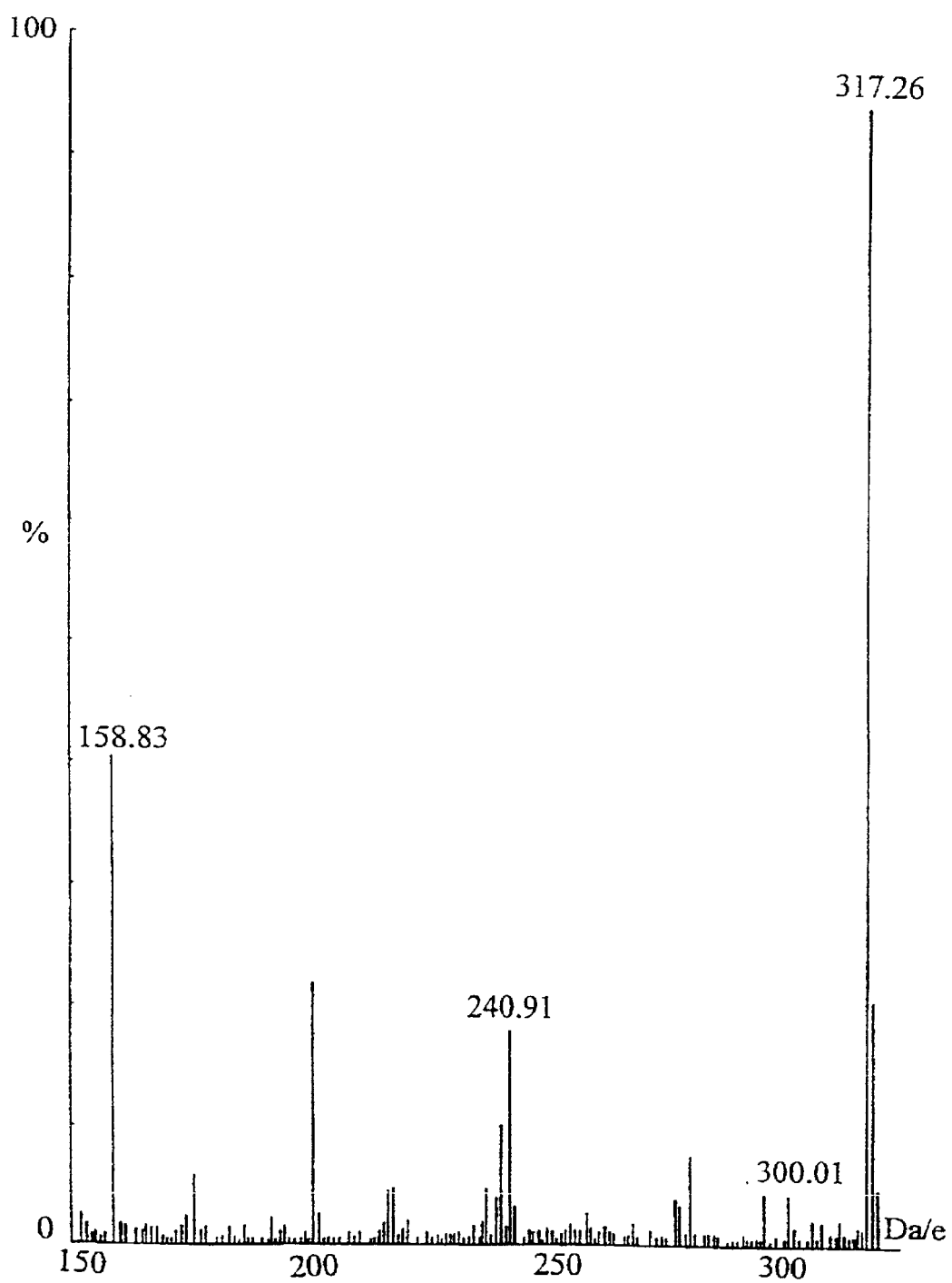

Mass spectroscopy (electron spray) analysis of the active fraction (FIG. 7) indicates the presence of a single compound with a molecular weight of 316 (317-1). Fragmentation of the molecule at cone voltage 30, 45 and 60 V is shown in FIG. 8 (a–c). The 159 molecular mass fragment may represent half the mass of the compound. Such a half mass fragmentation is characteristic to a double charged molecule (M/2e). In addition, double charged ions are mostly found in spectra of highly unsaturated compounds (e.g. aromatics or N-containing aromatics).

The mass and UV spectra, as well as the SDF behavior on RP-HPLC at different pH's, suggest that the active material is an aromatic charged composition of matter.

Example 3

Biological Experimental Procedures

Continuous Cell Lines

Cell lines included the human myelomonocytic cells HL-60, GM-CSF-dependent human myelomonocytic cells LK (established in the inventors' laboratory) and the murine monocytic cell line WEHI. Cell lines were maintained by sub-culturing every 3–4 days at $2.5 \times 10^5$ cell/ml in either alpha minimal essential or RPMI-1640 media (GIBCO, Grand Island, N.Y.) supplemented with 10–20% fetal calf serum (FCS) (Bio Labs Jerusalem, Israel). The cultures were incubated at 37° C., in a humidified atmosphere of 5% $CO_2$ in air. The concentration of viable cells was determined by the trypan blue exclusion technique. Total cell count was performed using a Coulter counter.

Cell Proliferation Assay

HL-60 or other cells were cultured at $1.3 \times 10^5$/ml in 24-well dish and medium containing 0.5% heat-inactivated FCS and various dilutions of the tested fractions. DNA synthesis was determined on day 4 by incorporation of $^3$[H]-thymidine (1 mci/150 μl) (5 mCi/mmol, ICN Radiochemicals, Irvine, Calif.) added 12 hrs before harvesting. One unit of SDF was defined as the amount per milliliter required for 50% decrease in $^3$H-thymidine incorporation.

Cell Differentiation Assays

Morphology: Cytospin (Shandon, Cheshire, UK) prepared slides were stained with May-Grunwald Giemsa. The percentage of macrophage-like cells was determined by scoring at least 100 cells.

Phagocytosis Tests

Polystyrene latex particles (3.2$\mu$ diameter) (Sigma, St. Louis. Mo.) were added on day 3 of the assay as follows: Human serum was diluted 1:1 with saline and filtered through a 0.45$\mu$ filter (to remove insoluble particles). Then, 5×10$^7$ beads were added per ml diluted serum and incubated for 30 min at 37° C. This suspension was added at 0.1 ml/ml culture. Following 24 hr incubation, the cells were collected, washed twice with medium (in order to remove free latex particles) and the percentage of phagocytic cells was determined by scoring at least 200 cells, under an inverted microscope. An automatic phagocytosis test was performed by adding fluorescent 2$\mu$ latex particles (Polyscience, Warrington. Pa.) to the culture as described. Following 24 hrs incubation, a sample was directly analyzed in the Fluorescence Activated Cell Sorter (FACSTAR Plus, Becton-Dickinson).

Primary Leukemic Cells

Cells were obtained from patients admitted to the Hematology department of The Hadassah Medical Center, Ein Karem, Israel. Peripheral blood (PB) and bone marrow (BM) cells were collected in preservative-free heparin. Mononuclear-enriched fractions were prepared by Ficoll Hypaque (Pharmacia. Milan, Italy) density gradient centrifugation, washed and frozen in liquid nitrogen. Prior to each experiment, cells were thawed and cultured at 1×10$^6$ cells/ml in alpha medium supplemented with 20% FCS and 10% conditioned medium from bladder carcinoma cell cultures (5637-CM).

Leukemic Cell Cloning

300–1000 cells/ml were seeded in semi-solid medium composed of 0.83% methyl-cellulose (Fisher Scientific company, Fair Lawn, N.J.) or 0.3% Bacto agar (Difco laboratories, Detroit, Mich.) in alpha medium supplemented with 10% FCS. Colony number was scored with an inverted microscope on day 8. In order to determine cellular maturation, single colonies were picked up with a fine capillary tube, smeared on a glass slide and stained.

Cloning of Normal Progenitors

Direct cloning: Peripheral bone mononuclear cells or BM cells obtained from normal volunteers were isolated by centrifugation on a gradient of Ficoll-Hypaque, and cloned in methylcellulose-containing alpha medium. For myeloid colonies, 30% FCS and CSF, in the form of 5637-CM or 100 U/ml GM-CSF, or IL-3 (Genetic institute, Cambridge, Mass.), 1% deionized BSA, 1×10$^{-5}$M 2-mercaptoethanol and 1.5 mM glutamine were added. For erythroid colonies, the culture included 30% FCS, 1% deionized BSA, 1.5 mM glutamine, 2-mercaptoethanol and 0.5–2 U/ml of erythropoietin (r-HuEPO, Cilag AG International, Zug Switzerland). One ml of the mixture containing either 2×10$^5$ BM or 5×10$^5$ PB cells was dispersed in 35 mm non-tissue culture dish (Falcon, Oxnared, Calif.). All semi-solid cultures were incubated at 37° C. in a sealed incubator in humidified atmosphere of 6% $O_2$, 7% $CO_2$ and 87% $N_2$. Colonies were scored with the aid of an inverted microscope. The cellular composition of colonies was confirmed by picking individual colonies, preparing a smear on a glass slide, and staining first with benzidine, and then, with Giemsa.

Indirect cloning: Cells were prepared as described for direct cloning, were first incubated for several days in liquid culture supplemented with or without the indicated growth factors or tested fraction, then washed. and cloned in semi-solid medium as described above.

Example 4

Effects of SDF or its Complex with CP on Different Cell Cultures

Effect on Normal Hemopoietic Cells

Expansion of normal hemopoietic progenitors—In order to test the effect of SDF on early and late normal hemopoietic progenitors a two-phase culture procedure was employed:

Phase 1 (Expansion phase)—Light density BM or PB cells were incubated for several days in liquid medium supplemented with SDF.

Phase 2 (Clonal phase)—At the end of phase 1, cells were harvested, washed and recultured in either semi solid medium or in liquid medium supplemented with either recombinant human late growth/differentiation factors like GM-CSF, Epo, or 5637-CM, which contains GM, G-CSF. IL-6, IL-1 and other cytokines, but not Epo. When BM or PB cells were incubated in Phase 1, for several days. with SDF as a sole factor, and then cloned (Phase 2) in SDF-free semi-solid medium, a significant expansion in the number of CFU-C was obtained (FIG. 9 A–B). The lineage specific differentiation of the colonies in Phase 2 depended on the late factor present, e.g., Epo for CFU-E and GM-CSF for CFU-GM. When phase 1 (expansion phase) was omitted and the cells were cloned directly in semi-solid medium, SDF by itself did not support colony development. When added to phase 2 with late factors, SDF had a small or no stimulatory effect (data not shown).

Like other early factors such as SCF, IL-1 and IL-6, SDF is mostly active in the expansion phase of pre CFU-C, and by itself cannot support the proliferation and differentiation of CFU-C. It probably stimulates the proliferation of pre CFU-C, possibly by direct stimulation of expansion of CD34$^+$ cells or by activation of accessory cells. Further proliferation and differentiation of CFU-C depends on the presence of late growth/differentiation factors.

Expansion of normal CD34$^+$ cells—Peripheral blood mononuclear cells were cultured in serum-containing liquid medium in the presence of SDF with no added cytokine. CD34$^+$ cells were enumerated by flow cytometry at the initiation of the culture and at different days thereafter. The results demonstrate an average 10-fold increase in CD34$^+$ following one week culture (FIG. 10).

Expansion of normal dendritic cells—As can be seen from FIG. 11, SDF induces commitment/expansion of PB CFU-dendritic. Using SDF in phase 1, up to 80% dendritic colonies in phase 2 were obtained from non-enriched PB mononuclear cells (FIG. 11).

Stimulation of hemopoietic progenitors from patients with pure red cell aplasia—Erythroid progenitors from patients with pure red cell aplasia fail to develop both in vivo and in vitro. However, when treated with SDF in phase 1, PB samples from affected children developed into large and red (hemoglobin-containing) colonies in phase 2 (FIG. 12).

Effect on Leukemic Cells

Acute myeloid leukemia—SDF was found to be active, at very low concentrations, on different myeloid leukemic established cell-lines, e.g. HL-60 promyelocytic leukemic cells (Table 2), WEHI monoblast-like cells (Table 3), LK, a GM-CSF dependent myeloid leukemic cell line established in the inventors' laboratory (Table 4), as well as on freshly explanted cells from patients with various forms of myeloid leukemia (Tables 5–6). In these, SDF-supplemented cultures. the leukemic population underwent differentiation into fully mature macrophages. The cells changed their shape into typical macrophage morphology (Table 2), acquired macrophage functions such as mobility in semi-solid agar medium (assayed by the change of the colony morphology from "tight" to "diffused" (Table 3), the ability to phagocyte foreign particles (Tables 2 and 6), and to produce "non-specific" esterase (NSE) activity (Table 6).

TABLE 2

Effects of SDF on HL-60 cells

| SDF dilution | Macrophage-like morphology | Phagocytosis (%) | Inhibition of thymidine uptake (%) | Inhibition of colon formation (%) |
|---|---|---|---|---|
| 1:100 | + + + + | 89 | 90 | 95 |
| 1:200 | + + + | 78 | 85 | 90 |
| 1:400 | + + + | 65 | 75 | 88 |
| 1:800 | + + | 57 | 70 | 72 |
| 1:1600 | + | 45 | 63 | 69 |
| 1:3200 | ± | 28 | 49 | 58 |
| 0 | − | | 0 | |

*HL-60, at $1.3 \times 10^5$ cells/ml, were cultured in medium supplemented with 0.5% heat inactivated FCS. Phagocytosis, cell morphology and DNA synthesis were determined on day 4. Morphology score of the results are indicates as follows: −(+ + + +) represent 80–100% macrophage-like cells, (+ + +) represent 60–80%, (+ +) represent 40–60%, (+) represent 15–40% and (±) represent 5–15% macrophage-like cells. For colonies, 600 cells were cloned per ml in a-MEM, 10% FCS and 0.3% Bacto agar and several dilutions of SDF.

For comparison, the effect of other growth and proliferation factors of the same cell lines was examined. As shown in the following table, SDF greatly inhibits colony formation.

TABLE 3

Effect of SDF and other growth and differentiation factors on

| | Colonies | | | |
|---|---|---|---|---|
| | Tight | Partially diffused | Diffused | Total |
| HL-60 cells | | | | |
| Control | 301 | 11 | 1 | 313 |
| G-CSF (1000 U/ml) | 325 | 12 | 0 | 337 |
| IL-1 (100 U/ml) | 332 | 8 | 1 | 341 |
| G-CSF + IL-1 | 338 | 14 | 0 | 352 |
| Retinoic acid | 0 | 49 | 114 | 163 |
| SDF dilution: | | | | |
| 1:200 | 0 | 2 | 5 | 7 |
| 1:400 | 0 | 10 | 2 | 12 |
| 1:800 | 2 | 17 | 16 | 35 |
| 1:1600 | 5 | 28 | 22 | 55 |
| WEHI cells | | | | |
| Control | 78 | 20 | 17 | 115 |
| G-CSF (100 U/ml) | 25 | 55 | 51 | 132 |
| IL-1 (100 U/ml) | 0 | 16 | 94 | 11 |
| G + IL-1 | 2 | 40 | 89 | 131 |
| SDF dilution: | | | | |
| 1:100 | 0 | 63 | 11 | 74 |
| 1:200 | 2 | 77 | 20 | 98 |
| 1:400 | 5 | 80 | 26 | 111 |
| 1:800 | 21 | 62 | 11 | 99 |

TABLE 3-continued

Effect of SDF and other growth and differentiation factors on

| | Colonies | | | |
|---|---|---|---|---|
| | Tight | Partially diffused | Diffused | Total |
| 1:1600 | 53 | 42 | 15 | 109 |
| 1:3200 | 43 | 32 | 12 | 87 |

*HL60 (600 cells/ml) and WEHI (300 cells/ml) were cloned as with described for Table 2. Cells in α-medium, 10% FCS and 0.3% Difco Bacto agar were plated with different dilutions of SDF, IL-1 G-CSF and retinoic acid. Colonies were classified according to their morphology as tight (undifferentiated), partially diffused (partially differentiated) and diffused (fully differentiated). The number of colonies was determined after 8 days, as the mean of the results obtained in two independent experiments.

TABLE 4

The effect of SDF on the proliferation of LK cells

| | Without GM-CSF | | With GM-CSF | |
|---|---|---|---|---|
| SDF dilution | CPM | Growth inhibition (%) | CPM | Growth inhibition (%) |
| Control | 4778 | 0 | 17247 | 0 |
| 1:100 | 1552 | 68 | 4700 | 73 |
| 1:200 | 2003 | 59 | 4980 | 72 |
| 1:400 | 2017 | 59 | 5081 | 71 |
| 1:800 | 1719 | 64 | 5739 | 67 |

*LK cells (a GM-CSF dependent myeloid leukemic cell line) were cultured at $5 \times 10^4$ cells/ml in α-MEM and 10% FCS. The cultures were supplemented with or without GM-CSF (100 U/ml) and different dilutions of SDF. DNA synthesis was determined on day 4 by incorporation of $^3$H-thymidine. The results are expressed as CPM/ml culture and percent of growth inhibition.

It is clear from the above that SDF is capable of inhibiting the growth of myeloid leukemia cells also in the absence of GM-CSF.

TABLE 5

(A)-(D)
The effect of SDF on freshly explauted AML cells

A: Patient 1 - M1/M2 cells

| | SDF | | SDF + GM-CSF | |
|---|---|---|---|---|
| SDF dilution | CPM | Inhibition (%) | CPM | Inhibition (%) |
| Control | 7000 | 0 | 11000 | 0 |
| 1:100 | 1540 | 78 | 1640 | 85 |
| 1:200 | 1435 | 79 | 2438 | 78 |
| 1:400 | 2296 | 67 | 2107 | 81 |
| 1:800 | 2892 | 59 | 3108 | 72 |
| 1:1600 | 4300 | 39 | 4834 | 57 |
| 1:13200 | 5971 | 15 | 5894 | 46 |

B: Patient 2 - M1 cells

| | CPM | | Inhibition (%) | | Phagocytic cells (%) | |
|---|---|---|---|---|---|---|
| SDF dilution | (−) CSF | (+) CSF | (−) CSF | (+) CSF | (−) CSF | (+) CSF |
| Control | 6000 | 12000 | 0 | 0 | 49 | 63 |
| 1:200 | 900 | 626 | 85 | 95 | 96 | 93 |
| 1:400 | 800 | 588 | 87 | 95 | 95 | 95 |
| 1:800 | 872 | N.D. | 86 | N.D. | 90 | N.D. |
| 1:1600 | 1000 | N.D. | 83 | N.D. | 85 | N.D. |

TABLE 5-continued (A)-(D)
The effect of SDF on freshly explauted AML cells

C: Patient 3 - AML M4 cells (Acute Monocytic Leukemia)

| Culture conditions | CPM | Inhibition (%) | Phagocytic cells (%) day 4 | day 7 |
|---|---|---|---|---|
| FCS 10% | 9840 | | 12 | 26 |
| FCS 10% + SDF 1:200 | 2767 | 72 | 45 | 70 |
| AML serum 10% | 14120 | | 5 | 10 |
| AML serum 10% + SDF 1:200 | 3800 | 73 | 15 | 50 |

*Primary AML cells were cultured at $1 \times 10^6$ cells/ml in a-MEM and 10% FCS or autologous serum with or without SDF (1:200 dilution). The cultures were labeled with $^3$H-thymidine after six days.

D: Patient 4 - Mixed AML-ALL cells

| Culture conditions | Sudan Black (%) | NSE* (%) | Phago-cells (%) |
|---|---|---|---|
| Prior to culture | 20 | 0 | 1 |
| After 6 days in culture FCS (10%) | 7 | 7 | 10 |
| FCS (10%) + SDF (1:200) | 8 | 37 | 50 |
| Autologous serum (10%) | 46 | 6 | 5 |
| Autologous serum (10%) + SDF (1:200) | 16 | 34 | 45 |

Primary mixed AML-ALL cells were cultured at $1 \times 10^6$ cells/ml as indicated. Cells were analyzed on the sixth day of culture.

In all four experiments, (A) to (D), non specific esterase and phagocytic cells were determined on the sixth day.

Upon exposure to SDF, as a result of terminal cell differentiation, the leukemic cells lost their ability for proliferation and self-renewal, as determined by thymidine uptake and cloning in semi-solid medium (Table 2 and FIG. 13).

Although full maturation occurred after 3–4 days, exposure to SDF for one day sufficed to induce irreversible commitment to terminal differentiation (Table 6), including the loss of self-renewal capacity.

TABLE 6

The effect of SDF on self renewal and commitment to differentiation of HL-60 cells

| Incubation with SDF (days) | No. of colonies per plate | Phagocytic cells (%) |
|---|---|---|
| 0 | 150 | 3 |
| 1 | 1 | 18 |
| 2 | 1 | 65 |
| 3 | 0 | 74 |

*HL-60 cells were incubated with SDF (1:200 dilution). After 1, 2 or 3 days, the cells were washed and $1 \times 10^3$ viable cells were plated in semi-solid culture. Remaining cells were replanted in suspension. Colony number was determined on day 7. Phagocytic capacity was determined on the sixth day.

Leukemic cells, such as HL-60 cells, inhibit the development of normal BM cells. However, when HL-60 cells were treated for 24 hrs with SDF, they lost their ability to inhibit normal hemopoietic development (Table 7).

TABLE 7

The effect of HL-60 cells on development of normal BM colonies

| | % of control (No. of BM colonies) |
|---|---|
| Control | 100% (320) |
| Untreated HL-60 cells | 8% (26) |
| SDF-treated HL-60 cells | 56% (180) |

*Viable HL-60 cells ($1 \times 10^5$) were incubated for 24 hours with or without SDF (1:200 dilution) and then plated in agar as an underlay of normal BM cells. The number of BM colonies was determined on day 12.

Chronic Myeloid Leukemia (CML)

The effect of SDF on the proliferation ability of cells derived from chronic myeloid leukemic patients (CML) was also examined by the inventors (Table 7). SDF was cultured with CML colony forming cells (CFU-C) in a direct cloning procedure, utilizing a semi-solid culture and in an indirect cloning Procedure (two phase culture), as described herein before. These Cells retained their ability to differentiate but showed abnormal proliferation pattern. Therefore, is was concluded that SDF is capable of inhibiting the potential of these progenitors to proliferate and to develop colonies. When CML cells were grown in liquid cultures, SDF had no apparent toxicity. These cultures contained mainly myeloid precursors at various stages of maturation.

These results suggest that SDF inhibits early (pre-CFU-C) CML progenitors (either by direct inhibition of their proliferation or indirectly by inducing rapid differentiation), but has no deleterious effect on the more mature cells.

TABLE 8

SDF effect on CML Colony Forming Cells (CFU-C) Inhibition (%)

| Fraction dilution | Direct cloning | Indirect cloning |
|---|---|---|
| 1:100 | 100 | 80 |
| 1:200 | 100 | 60 |
| 1:500 | 70* | 20 |
| 1:1000 | 40* | 0 |

*Small colonies compared to control. Number of colonies was determined on day 14 and the results are expressed as percent of inhibition compared with the control.

As noted above, The effect of SDF was assayed on CML colony forming cells by the direct and indirect colony assays. For direct cloning, $0.5 \times 10^6$ cells/ml were cultured in semi solid medium supplemented with GM-CSF and Epo, with or without the indicated dilution of SDF. For indirect cloning, $0.5 \times 10^6$ cells/ml were cultured first in liquid medium with the indicated dilution's of SDF. After 3 days, non adherent cells were recovered, washed, and assayed for CFU-C in semi solid medium supplemented only with GM-CSF and Epo.

Effect of SDF on Normal Hemopoietic Progenitors

Different growth factors e.g. G-CSF, GM-CSF are currently used in bone marrow transplantation. They have been shown to shorten neutrophil recovery time after transplantation (and chemotherapy) by stimulating myeloid progenitors. However, since myeloid leukemic cells have receptors for these factors, the proliferation of residual malignant cells is also stimulated. The following reveals that SDF by itself or in combination with GM-CSF potentiates the proliferation of normal progenitors, but inhibits "spontaneous" and GM-CSF stimulated proliferation of myeloid leukemic cells, thus having a dual effect: eradication of leukemic cells concomitantly with stimulation of the normal ones.

Example 5
Effect of SDF on Angiogenesis

The inventors have found that highly purified plasma derived SDF contains a potent inhibitory activity on endothelial cell proliferation, in vitro (Table 8).

TABLE 9

Effect of SDF on proliferation of endothelial cells

| Fraction | CPM |
|---|---|
| control | 35000 |
| S-Sepharose derived fraction dilution | |
| 1:1000 | 15000 |
| 1:500 | 9000 |
| 1:250 | 5000 |
| SDS gel derived fraction | |
| dilution | |
| 1:100 | 3500 |
| 1:50 | 1200 |
| 1:25 | 550 |

*Endothelial cells derived from bovine aorta were seeded in 1 ml aliquots per well (5000 cells/ml) into 24-well cluster dishes. The culture medium was supplemented with 10% heat inactivated horse serum. After 5 hr. incubation, 40 µl of buffer or buffer supplemented with various concentration of the SDF-containing fractions were added to each well. Following 4 days of incubation, the cultures were pulsed labeled with $^3$H-thymidine for 20 hrs and then harvested. The results are expressed as counts per minute (CPM).

Example 6
Effect of PQQ on Hemopoietic Progenitor Cells

The inventors have found that PQQ and related compounds induce differentiation in myeloid leukemic cells and stimulate the growth of early hemopoietic progenitor cells. The described effect is exemplified in Table 10.

TABLE 10

The effect of PQQ on the proliferation of HL60 cells

| Concentration (µg/ml) | Growth inhibition (%) |
|---|---|
| 5 | 60 |
| 1 | 40 |
| 0.5 | 40 |
| 0.1 | 30 |
| 0.05 | 30 |
| 0.01 | 0 |

Further, the effect of PQQ on normal hemopoietic progenitor cells in an indirect cloning system was examined (Table 11).

TABLE 11

Effect of PQQ in an indirect cloning system

| Concentration (µg/ml) | Colony No. |
|---|---|
| 5 | 148 |
| 1 | 130 |
| 0.1 | 109 |
| 0.01 | 89 |
| 0 | 70 |

What is claimed is:

1. A biologically active composition comprising ceruloplasmin and a serum-derived composition (SDF) having a low molecular weight, being electrically charged at acidic pH and having absorption at 280 nm.

2. The biologically active composition of claim 1, wherein a concentration of said serum-derived composition is selected capable of inducing terminal cell differentiation of leukemic cells.

3. The biologically active composition of claim 1, wherein a concentration of said serum-derived composition is selected capable of inducing loss of proliferation and self cell renewal in leukemic cells.

4. The biologically active composition of claim 1, wherein a concentration of said serum-derived composition is selected capable of stimulating the proliferation of early, normal progenitor cells.

5. The biologically active composition of claim 1, wherein a concentration of said serum-derived composition is selected capable of inhibiting enhanced angiogenesis.

6. A pharmaceutical composition comprising, as active ingredients, ceruloplasmin and a serum-derived composition (SDF) having a low molecular weight, being electrically charged at acidic pH and having absorption at 280 nm, and a pharmaceutically acceptable additive.

7. The pharmaceutical composition of claim 6, wherein a concentration of said serum-derived composition is selected capable of inhibiting enhanced angiogenesis.

8. The pharmaceutical composition of claim 6, wherein a concentration of said serum-derived composition is selected capable of inducing remission in tumor tissue.

9. The pharmaceutical composition of claim 6, wherein a concentration of said serum-derived composition is selected capable of expanding hematopoictic normal stem and progenitor bone marrow transplants.

* * * * *